United States Patent
Ma et al.

(10) Patent No.: US 11,339,179 B2
(45) Date of Patent: May 24, 2022

(54) PREPARATION FOR NATURAL PRODUCT TRABECTEDIN

(71) Applicant: CE Pharm Co., Ltd., Taizhou (CN)

(72) Inventors: Dawei Ma, Shanghai (CN); Weiming He, Shanghai (CN); Zhigao Zhang, Shanghai (CN)

(73) Assignee: CE Pharm Co., Ltd., Zhejiang Province (CN)

( * ) Notice: Subject to any disclaimer, the term of this patent is extended or adjusted under 35 U.S.C. 154(b) by 0 days.

(21) Appl. No.: 16/772,888

(22) PCT Filed: Dec. 11, 2018

(86) PCT No.: PCT/CN2018/120340
§ 371 (c)(1),
(2) Date: Jun. 15, 2020

(87) PCT Pub. No.: WO2019/114704
PCT Pub. Date: Jun. 20, 2019

(65) Prior Publication Data
US 2021/0163500 A1 Jun. 3, 2021

(30) Foreign Application Priority Data
Dec. 13, 2017 (CN) .......................... 201711331695.1

(51) Int. Cl.
*C07D 515/22* (2006.01)
(52) U.S. Cl.
CPC .................. *C07D 515/22* (2013.01)
(58) Field of Classification Search
CPC .................................................. C07D 515/22
See application file for complete search history.

(56) References Cited

U.S. PATENT DOCUMENTS

| | | |
|---|---|---|
| 7,767,659 B2 | 8/2010 | Barrasa et al. |
| 7,795,260 B2 | 9/2010 | Barrasa et al. |
| 7,947,671 B2 | 5/2011 | Barrasa et al. |
| 8,058,435 B2 | 11/2011 | Zhu et al. |
| 9,428,524 B2 | 8/2016 | Martin Lopez et al. |

FOREIGN PATENT DOCUMENTS

| | | |
|---|---|---|
| CN | 104974056 A | 10/2015 |
| CN | 104974056 B | 1/2017 |
| WO | 03066638 A2 | 8/2003 |
| WO | 2007045686 A2 | 4/2007 |
| WO | 2011147828 A1 | 12/2011 |

OTHER PUBLICATIONS

Chen, R. et al.,"Asymmetric Total Synthesis of (−)-Jorunnamycins A and C and (−)-Jorumycin from L-Tyrosine," J. Nat. Prod. 76(9):1789-1795, doi.org/10.1021/np400538q (Aug. 27, 2013).
Corey, E. J. et al., "Enantioselective Total Synthesis of Ecteinascidin 743," J. Am. Chem. Soc. 118:9202-9203 (1996).
Du, E. et al., "Asymmetric total synthesis of three stereoisomers of (−)-renieramycin G and their cytotoxic activities," Tetrahedron 71:4296-4303 (2015).
Jia, J. et al., "Asymmetric synthesis of (−)-renieramycin T," Org. Biomol. Chem., The Royal Society of Chemistry DOI: 10.1039/c6ob01064d (2016).
International Search Report (ISR) of ISA/CN in PCT/CN2018/120340, dated 19, 2019. (in English and Mandarin).

*Primary Examiner* — Paul V Ward
(74) *Attorney, Agent, or Firm* — Law Offices of Nisan Steinberg

(57) ABSTRACT

The present invention provides a preparation method for a natural product Trabectedin. Specifically, the present invention provides a preparation method for Et-743. In the method, tyrosine is used as an initial substrate, and after 26 steps of reaction, the Et-743 is synthesized. Raw materials and agents used in the synthetic route can all easily be obtained, reaction conditions are relatively mild, and preparation in large scale can be implemented.

8 Claims, No Drawings

PREPARATION FOR NATURAL PRODUCT TRABECTEDIN

CROSS-REFERENCE TO RELATED APPLICATIONS

This is a U.S. national phase application under 35 U.S.C. § 371 of Patent Cooperation Treaty Application No. PCT/CN2018/120340, filed Dec. 11, 2018, which claims priority from Chinese Patent Application Serial No. 201711331695.1, filed on Dec. 13, 2017, and which incorporates by reference those PCT and Chinese applications in their entireties.

FIELD OF THE INVENTION

The present invention relates to the field of synthesis. Specifically, the present invention provides a method for preparing natural product Trabectedin.

BACKGROUND OF THE INVENTION

Trabectedin (ecteinascidi-743, Et-743) is a marine natural product with an extremely complex structure from the marine tunicate animal mangrove Ecteinascidia turbinata. Since its approval in the EU in 2007 for the treatment of advanced soft tissue tumors, Trabectedin has achieved hundreds of millions of dollars in sales due to its remarkable efficacy. As the first modern marine drug, the anti-tumor activity of Trabectedin is 1-3 orders of magnitude higher than that of the currently widely used anti-tumor drugs in clinical practice. It is currently considered to be the most effective drug for the treatment of ovarian cancer. Spanish company Zeltia Pharma found that the compound exhibits significant effects on rectal cancer, breast cancer, lung cancer, melanoma, etc.

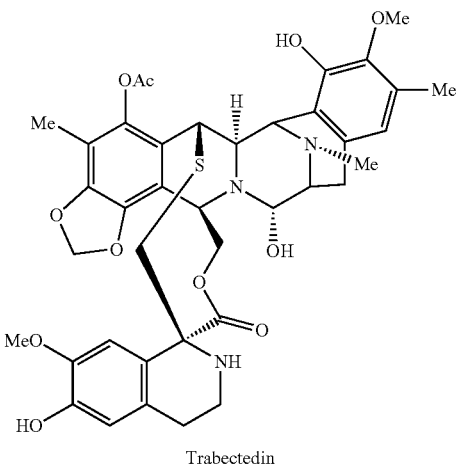

(Et 743)

Trabectedin

Studies found that the highest amount of Trabectedin (Et-743) extracted from sea squirts is 0.0001%. This makes it hardly possible to directly obtain the compound from nature drug source. Several synthetic routes have been reported, of which mainly are started from sesame phenol or its derivatives. For example, the route developed by Prof. E. J. Corey comprises 43 steps in total, the yield of which was 0.53% (J. Am. Soc, 1996, 118, 9202-9203.); and the route provided by Prof. Fukuyama comprises 45 steps in total, while the yield was 0.78%. Due to the long route and low total yield, and the poor operability of some steps, the application of these synthetic routes into production is also extremely limited.

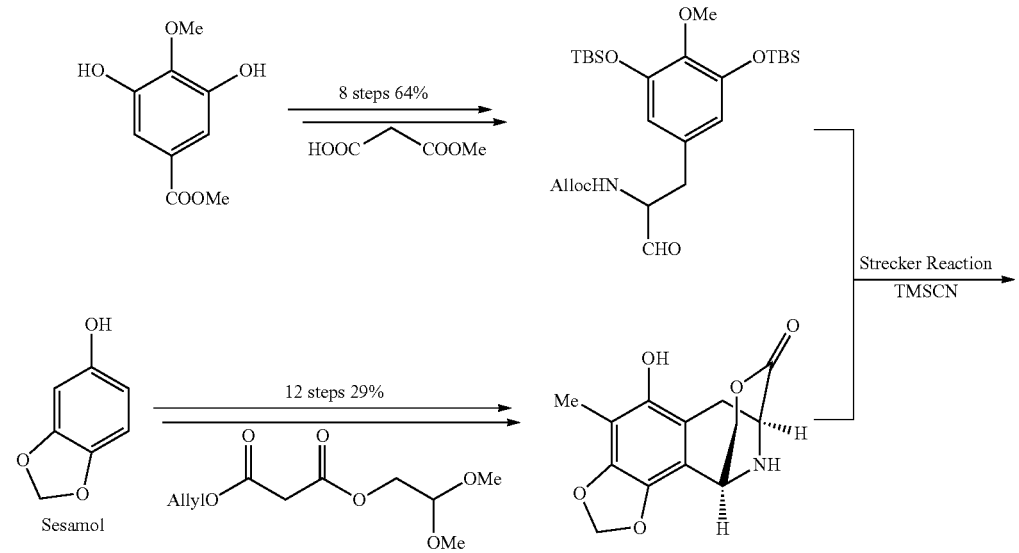

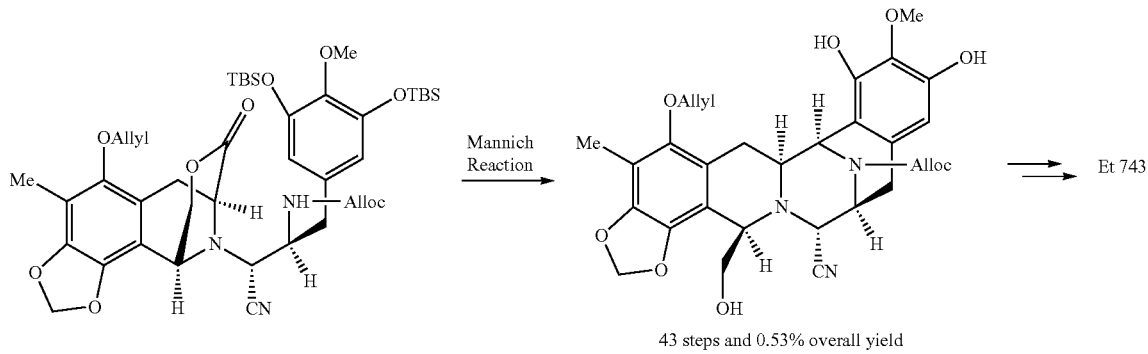
E.J. Corey, *J. Am. Chem. Soc,* 1996, 118, 9202-9203.
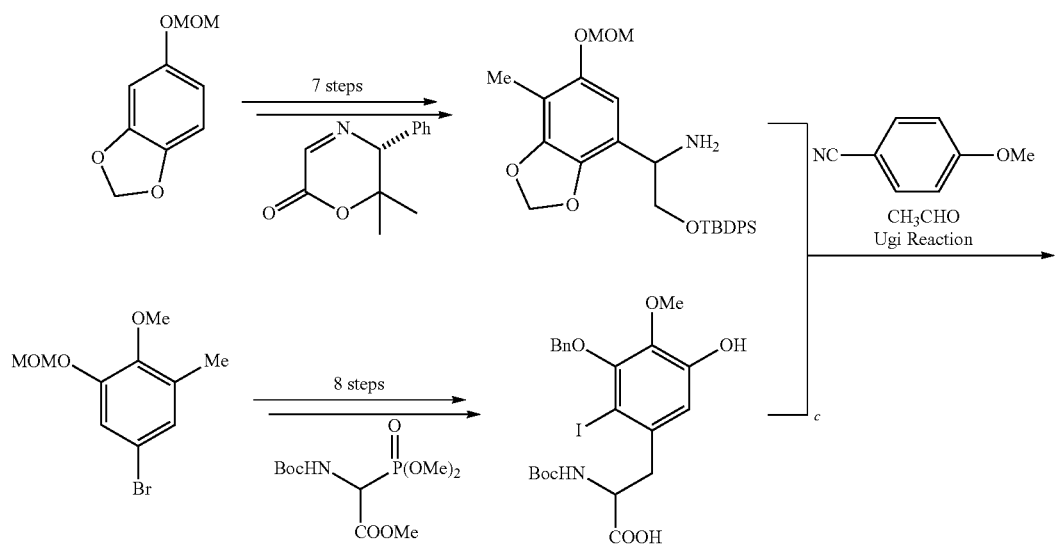
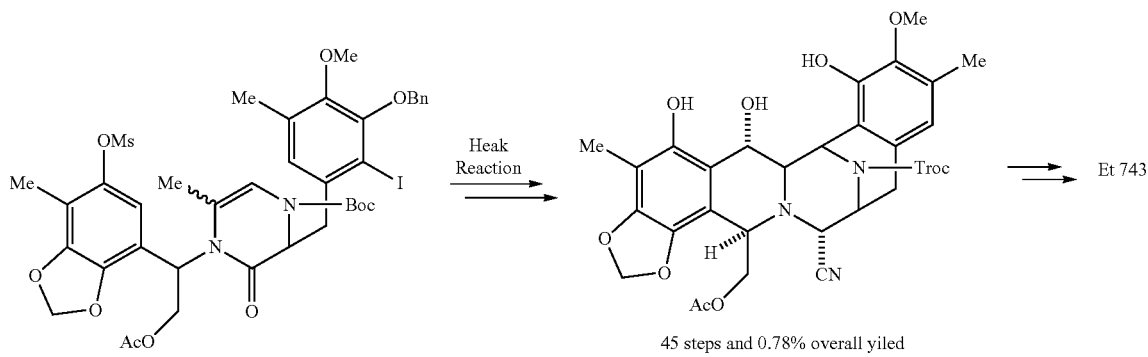
T. Fukuyama, *J. Am. Chem. Soc,* 2002, 124, 6552-6554.

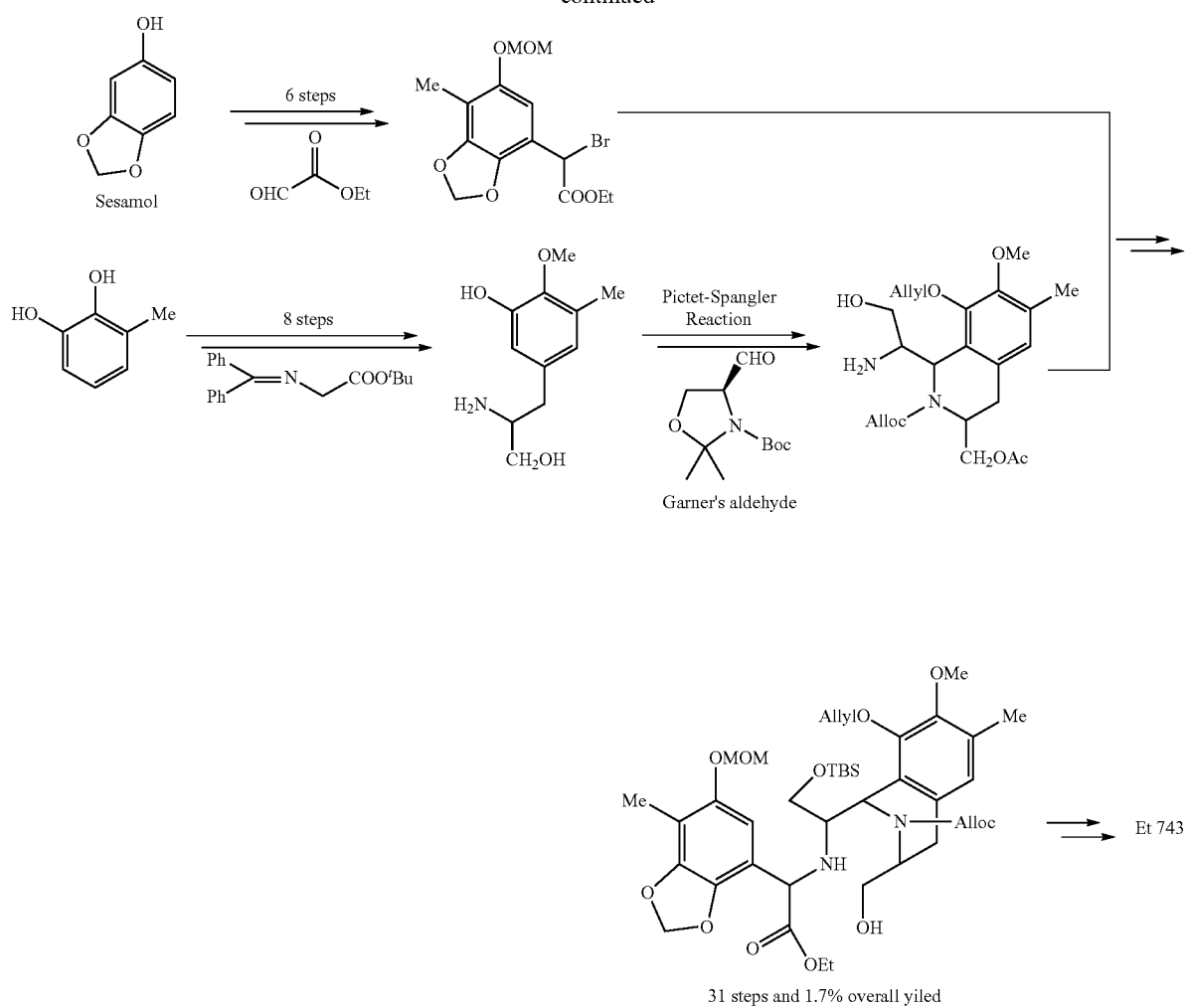
Jieping Zhu, *J. Am. Chem. Soc.* 2006, 128, 87-89
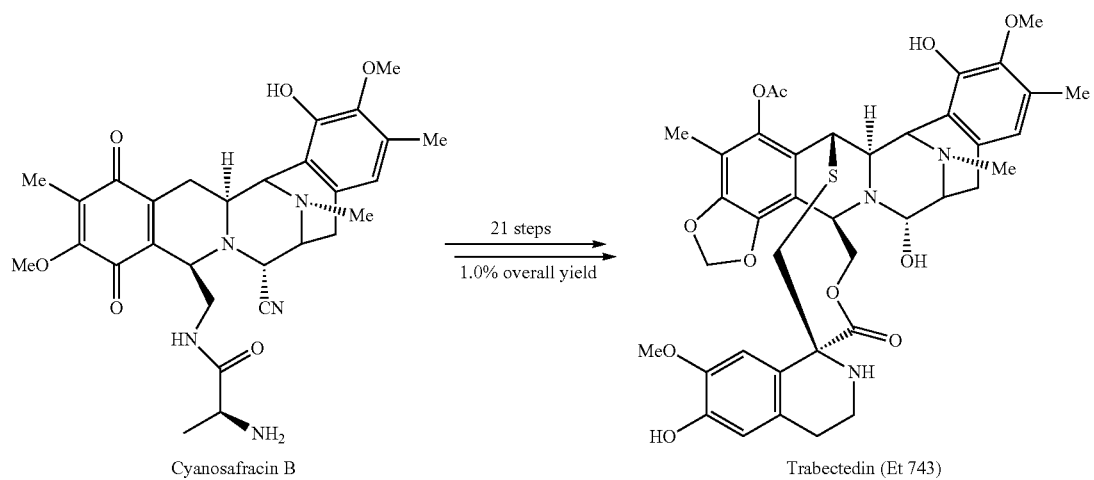

Currently, the drug is obtained through semi-synthesis by using cyanosafracin B as a raw material, which is obtained from *Pseudomonas fluorescens* by fermentation. Even if the method is a semi-synthesis route, it still needs 22 steps of reaction and the total yield is only 1.0%. Such a method for obtaining the compound makes the Trabectedin production very costly.

In summary, there is still a lack of a low-cost, high-efficiency method for preparing Trabectedin in this field.

SUMMARY OF THE INVENTION

The object of the present invention is to provide a low-cost, high-efficiency method for preparing Trabectedin.

In the first aspect of the present invention, a method for preparing Et-743 is provided.

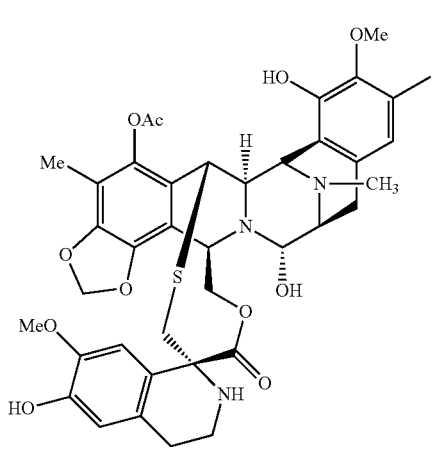

Et-743 wherein it comprises the steps:

(a) reacting compound 9 with compound 16 to obtain compound 18:

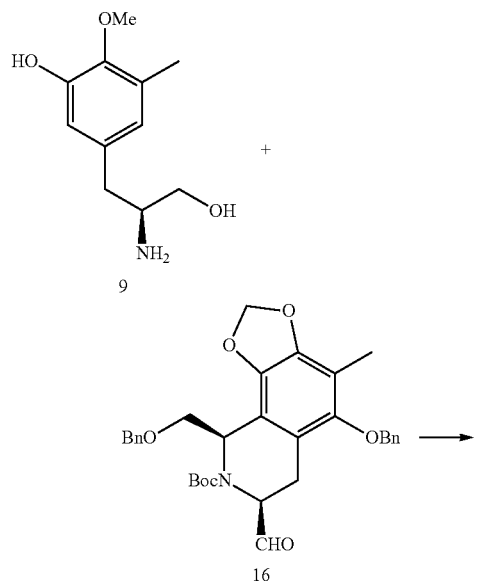

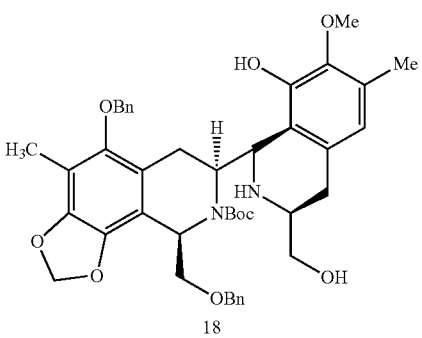

18

(b) subjecting compound 18 to the following reaction to obtain compound 19:

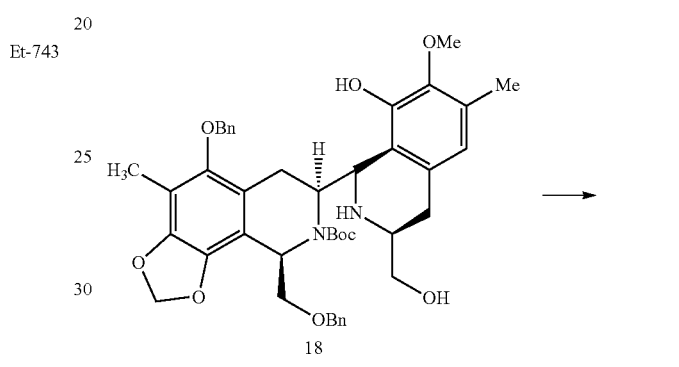

18

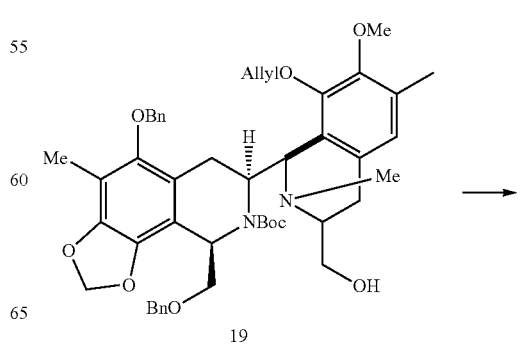

19

(c) subjecting compound 19 to the following reaction to obtain compound 20:

19

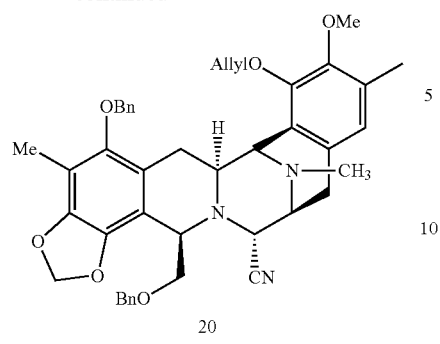
20
(d) subjecting compound 20 to the following reaction to obtain compound 21:
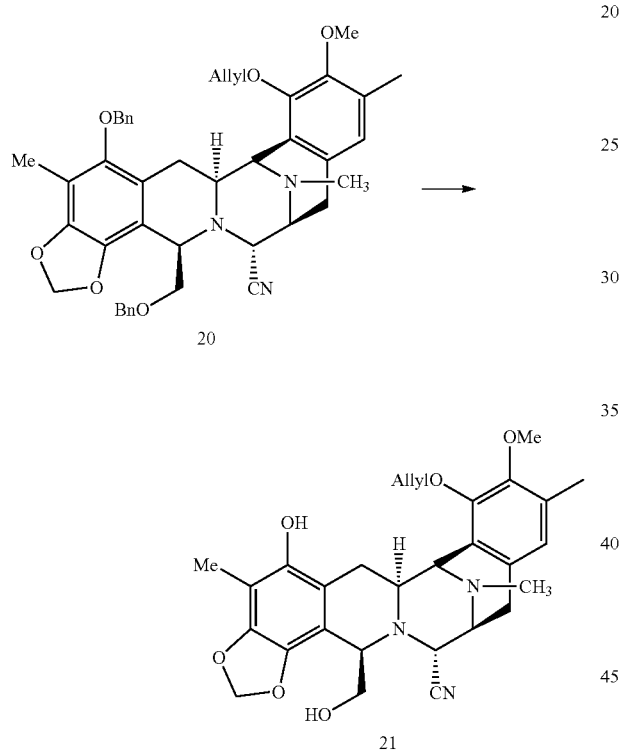
(e) subjecting compound 21 to the following reaction to obtain compound 22:
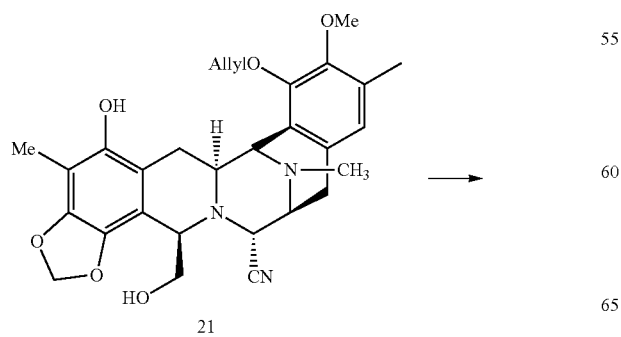
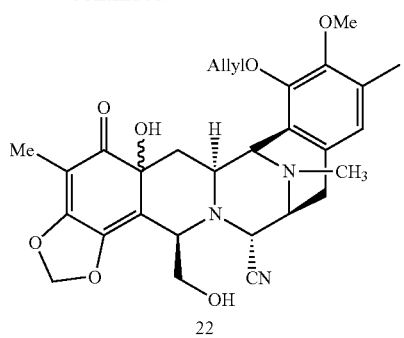
22
(f) reacting compound 22 with
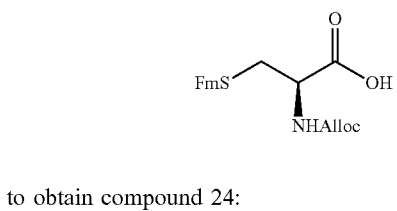
to obtain compound 24:
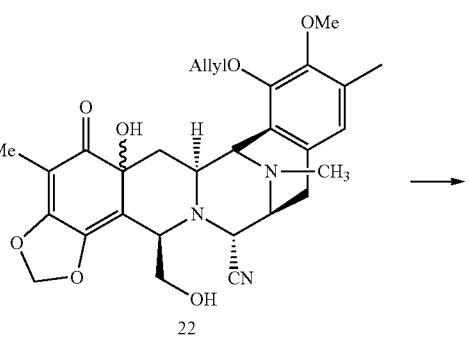
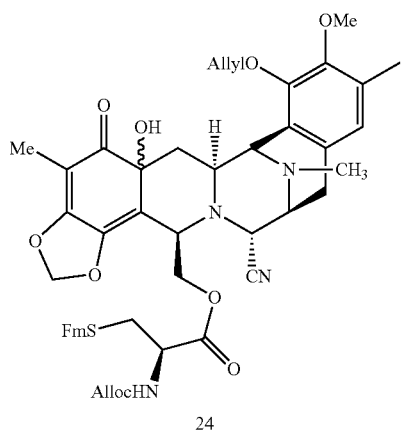
24

(g) subjecting compound 24 to the following reaction to obtain compound 25:

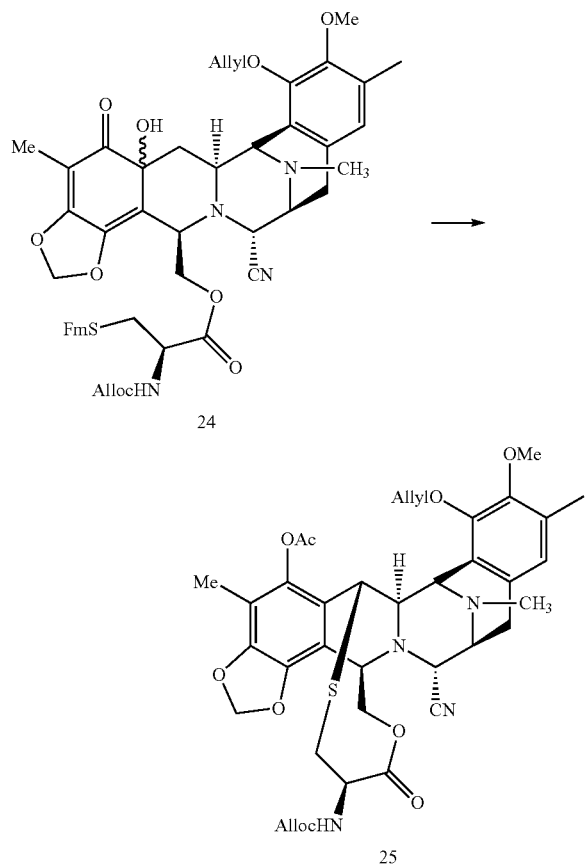

and preparing Et-743 from compound 25.

In another preferred example, in the step (a), the reaction is performed in an inert solvent (preferably toluene:DCM:TFE=2.7:1:1), in the presence of AcOH and 4A MS, and at 70° C. to obtain compound 18.

In another preferred example, in the step (b), the reaction comprises: (1) conducting a reaction in CH$_3$CN/THF mixed solvent, and in the presence of HCHO, NaBH$_3$CN and AcOH, then (2) conducting a reaction in acetone solvent with allylBr in the presence of K$_2$CO$_3$ under reflux to compound 19.

In another preferred example, in the step (c), the reaction comprises (1) after reacting under Swern oxidation conditions, reacting DIPEA with compound 19 in DCM, and then with TMSCN to obtain compound 20.

In another preferred example, in the step (d), compound 20 with BCl$_3$ in DCM at −80° C., and then with TMSCN to obtain compound 21.

In another preferred example, in the step (e), compound 21 is subjected to a reaction with (PhSeO)$_2$O in DCM at −10° C. to obtain compound 22.

In another preferred embodiment, in the step (f), in the presence of EDCI and DMAP, compound 22 is subjected to a reaction with

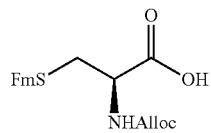

in dichloromethane to obtain compound 24.

In another preferred example, in the step (g), the reactions are sequentially performed in (1) DMSO solvent, reacting compound 24 with Tf$_2$O; (2) reacting with DIPEA at 0° C.; (3) reacting with tBuOH at 0° C.; (4) reacting with

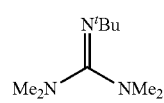

at room temperature; and (5) reacting with Ac$_2$O at room temperature to obtain compound 25.

In the second aspect of the present invention, a method for preparing Et-743 is provided:

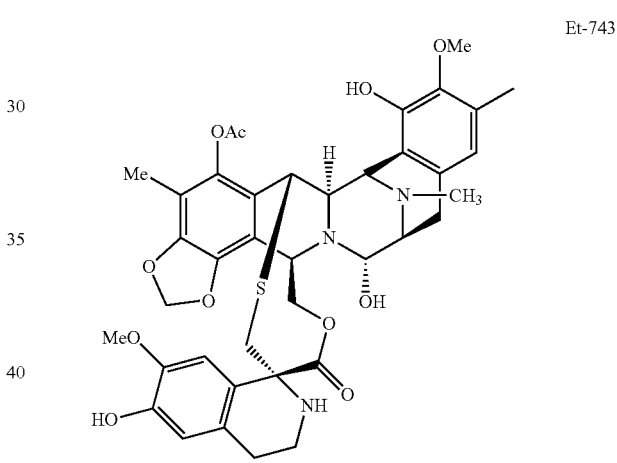

wherein it comprises the steps:

(g) subjecting compound 24 to the following reaction to obtain compound 25:

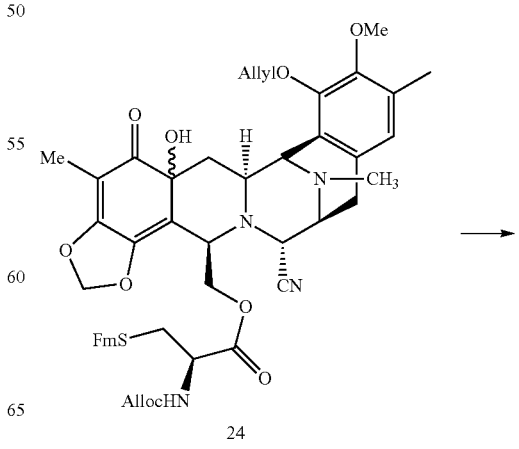

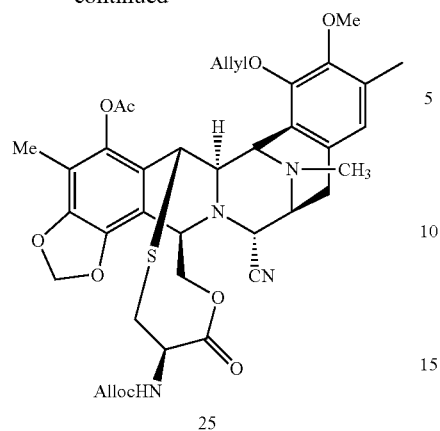

25 and preparing Et-743 from compound 25.

In another preferred example, in the step (g), the reactions are sequentially performed in (1) DMSO solvent, reacting compound 24 with Tf₂O; (2) reacting with DIPEA at 0° C.; (3) reacting with tBuOH at 0° C.; (4) reacting with

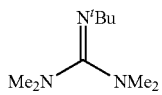

at room temperature; and (5) reacting with Ac₂O at room temperature to obtain compound 25.

In another preferred example, the preparation method includes the following steps:

Deprotecting the compound 25 to obtain compound 26:

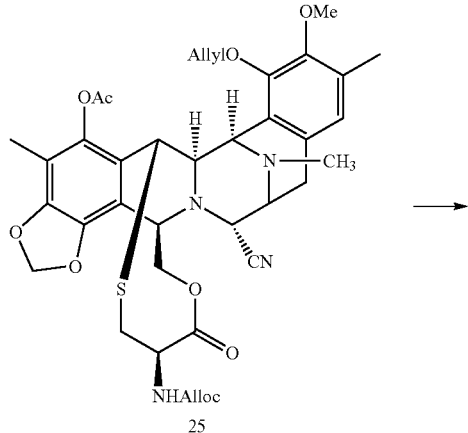

25

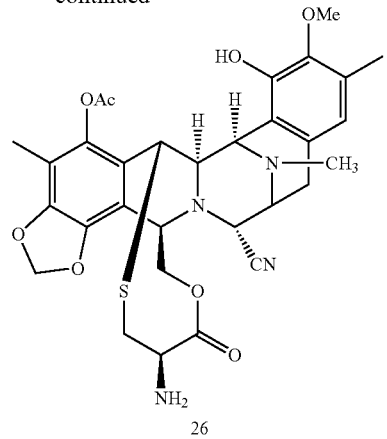

26

Preferably, the step comprises: in DCM, in the presence of AcOH, reacting Pd(PPh₃)₄ and Bu₃SnH with compound 25 to obtain compound 26.

In another preferred example, the preparation method further includes the following steps:

Oxidating compound 26 to obtain compound 28:

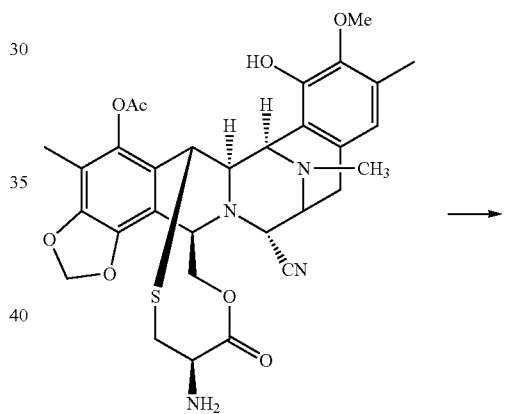

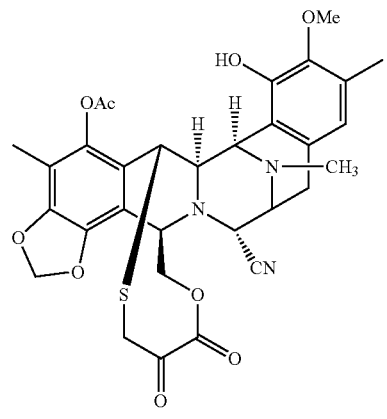

28

Preferably, the step includes (1) reacting compound 25 with

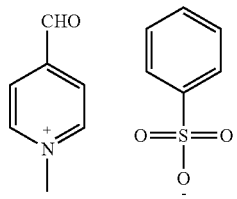

27 at room temperature in DMF, (2) continuously reacting with DBU, and (3) reacting with oxalic acid to obtain compound 28.

In another preferred example, the preparation method further includes the following steps:

reacting compound 28 with compound 29 to obtain compound 30:

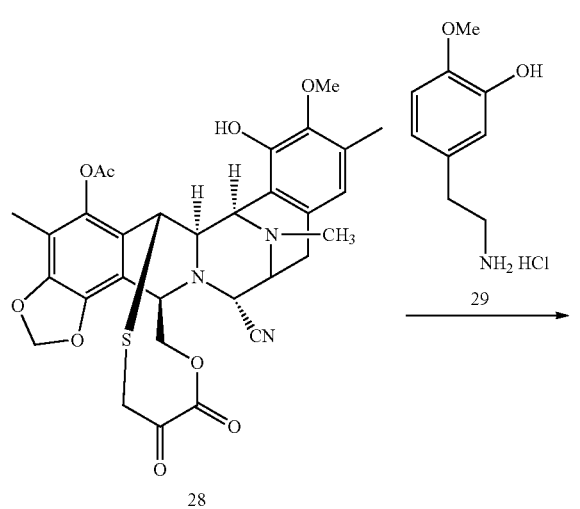

28

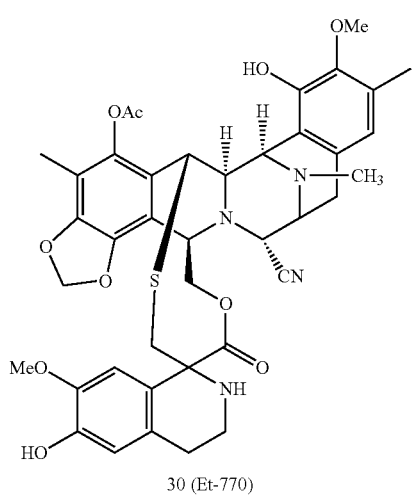

30 (Et-770)

Preferably, the step includes (1) reacting compound 28 with compound 29 in absolute ethanol in the presence of NaOAc to obtain compound 30.

In another preferred example, the preparation method further includes the following steps:

subjecting compound 30 to the following reaction to provide compound 31 (Et-743):

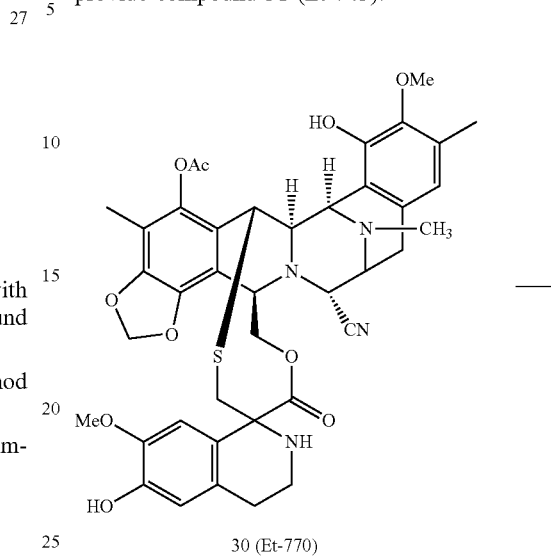

Preferably, the step includes (1) reacting compound 30 with AgNO$_3$ in an acetonitrile/water mixed solvent to obtain compound 31.

In the third aspect of the present invention, an intermediate compound of Et-743 is provided, which is selected from the group consisting of:

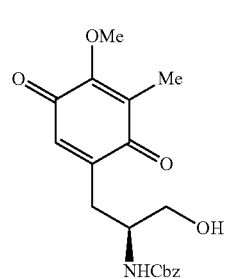

10

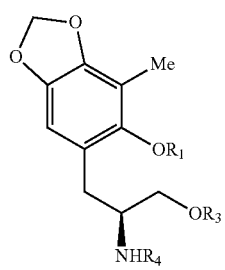

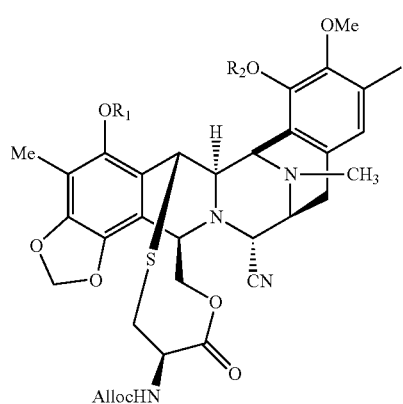

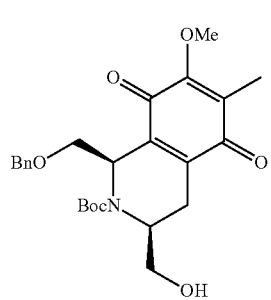

wherein
R₁ is selected from the group consisting of H, Bn-, allyl and $R_2$ is selected from the group consisting of H, Bn- and allyl;
$R_3$ is selected from the group consisting of H and Ac;
$R_4$ is selected from the group consisting of Cbz and R is selected from the group consisting of H and OH.

In the forth aspect of the present invention, a method for the preparation of compound of formula 16 is provided, wherein the method comprises the steps:
(vi) subjecting compound 15 to the following reaction to obtain compound 16:

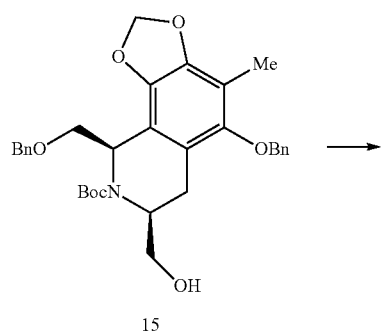

15

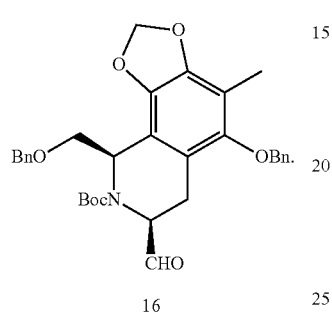

16

In the fifth aspect of the present invention, a method for the preparation of compound of formula 15 is provided, wherein the method comprises:

(i) subjecting compound 10 to the following reaction to obtain compound 11:

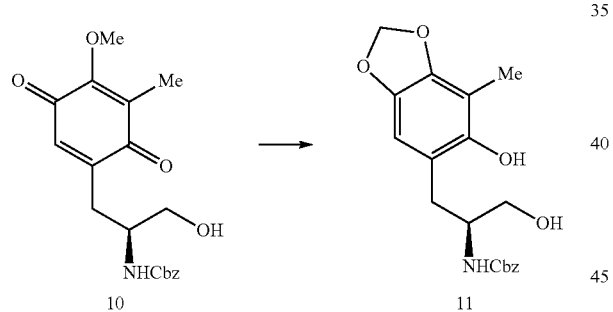

(ii) subjecting compound 11 to the following reaction to obtain compound 12:

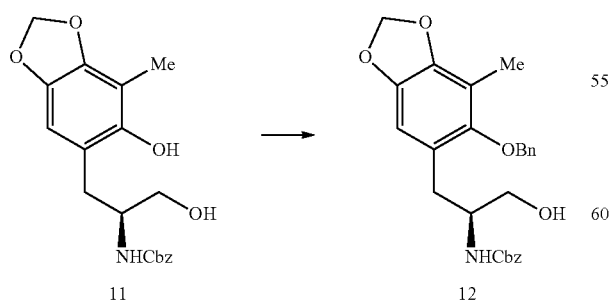

(iii) subjecting compound 12 to the following reaction to obtain compound 13:

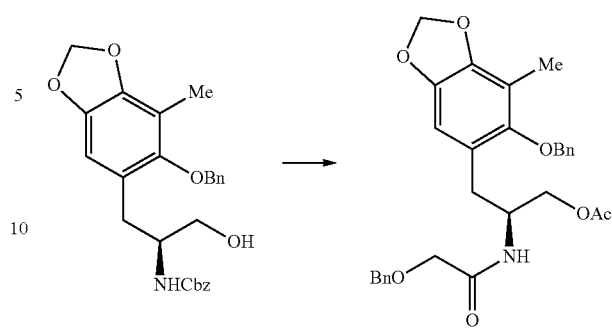

(iv) subjecting compound 13 to the following reaction to obtain compound 14:

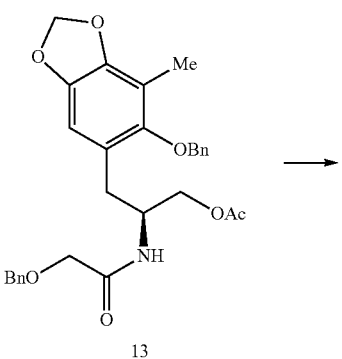

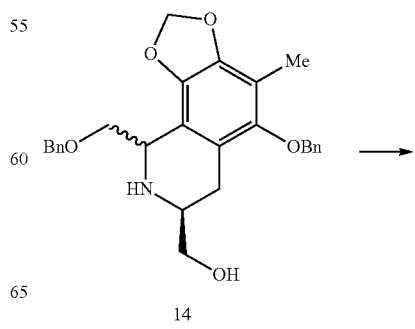

(v) subjecting compound 14 to the following reaction to obtain compound 15:

21
-continued
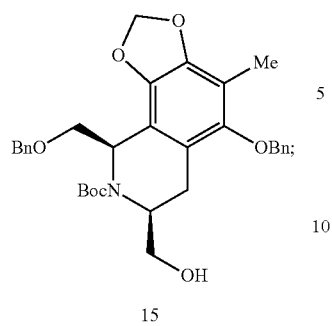
15
or the method comprises the following steps:
(i-a) subjecting compound 9 to the following reaction to obtain compound 32:
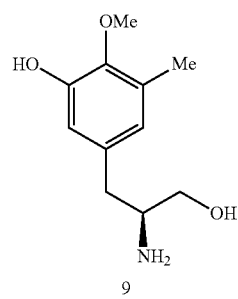
9
(ii-a) subjecting compound 12 to the following reaction to obtain compound 33:
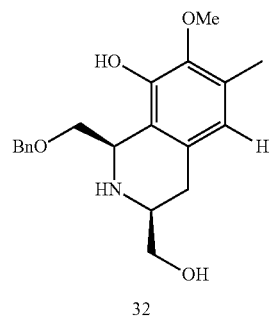
32
22
-continued
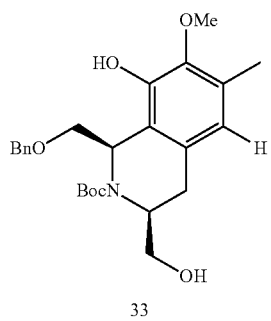
33
(iii-a) subjecting compound 33 to the following reaction to obtain compound 34:
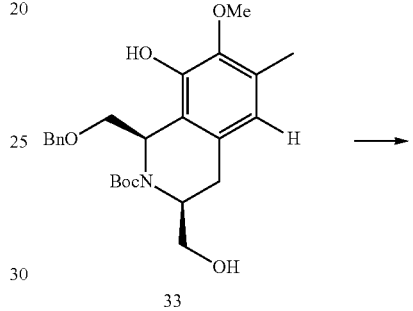
33
(iv-a) subjecting compound 34 to the following reaction to obtain compound 35.
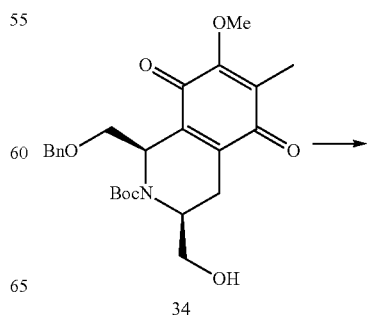
34

-continued

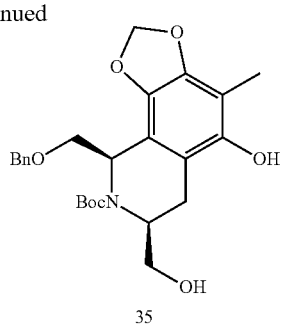
35

(v-a) subjecting compound 35 to the following reaction to obtain compound 15:

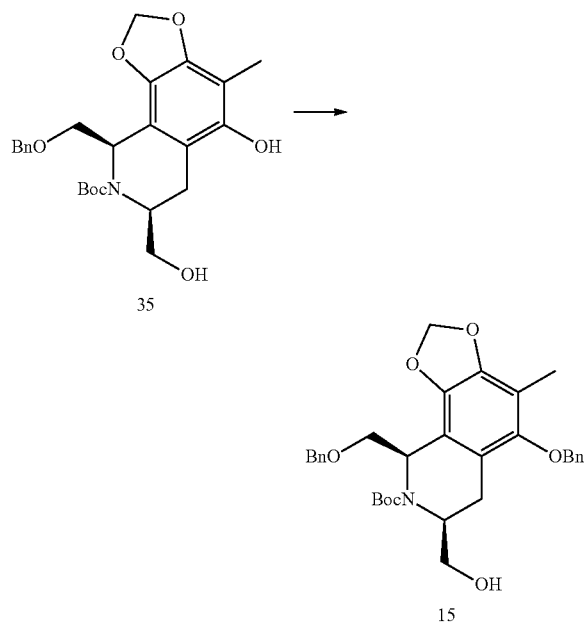

In another preferred example, in the step (i), the method includes: under blue light, reacting compound 10 in an inert solvent (preferably THF) to provide compound 11.

In another preferred example, in the step (ii), the method includes: conducting a reaction with BnBr in the presence of $K_2CO_3$ to obtain compound 12; preferably, the method is carried out at 55-65° C. in acetone solvent.

In another preferred example, in the step (iii), the method includes: (1) conducting a reaction in the presence of NaOH, in MeOH solvent at 100° C.; (2) in DCM solvent, reacting with

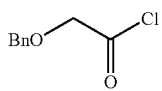

in the presence of $NEt_3$; (3) in the presence of $NEt_3$, reacting with AcCl to obtain compound 13.

In another preferred example, in the step (iv), the method includes: (1) conducting a reaction in the presence of $POCl_3$, at 80° C. in $CH_3CN$; (2) at 0° C., reacting with $NaBR_4$ to obtain compound 14.

In another preferred example, in the step (v), the method includes: reacting with $(BOC)_2O$ in the presence of $NEt_3$ to obtain compound 15.

In another preferred example, in the step (vi), the method includes: oxidizing compound in the presence of Swern oxidant to obtain compound 16.

In another preferred example, in the step (i-a), the method includes: in an inert solvent (preferably DCM/TFE=7:1), reacting the compound 9 with $BnOCH_2CHO$ to obtain compound 32. Preferably, the method is carried out in the presence of AcOH at 0° C., and in the presence of 4A molecular sieve.

In another preferred example, in the step (ii-a), the method includes: in an inert solvent (preferably DCM), in the presence of NEt3, reacting $Boc_2O$ with compound 32 to obtain compound 33.

In another preferred example, in the step (iii-a), the method includes: in an inert solvent (preferably $CH_3CN$), reacting the compound 33 with Salcomine oxidant and oxygen to obtain the compound 34.

In another preferred example, in the step (iv-a), the method includes: under blue light, reacting compound 34 in an inert solvent (preferably THF) to provide compound 35.

In another preferred example, in the step (v-a), the method includes: reacting compound 35 in an inert solvent (preferably acetone) at 65° C. to obtain compound 15; and preferably, the reaction was carried out in the presence of BnBr and $K_2CO_3$.

In another preferred example, the method further comprises a step:

subjecting compound 8 to the following reaction to obtain compound 10:

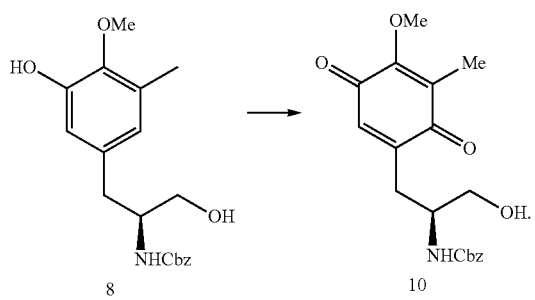 [SMILES: COc1c(C)cc(C[C@@H](CO)NC(=O)OCc2ccccc2)cc1O ; COC1=C(C)C(=O)C(C[C@@H](CO)NC(=O)OCc2ccccc2)=CC1=O]

In another preferred example, the reaction comprises: in $CH_3CN$, oxidizing compound 8 with Salcomine reagent/$O_2$ at room temperature to obtain compound 10.

In another preferred example, the compound 8 is prepared by using tyrosine as a raw material.

In the sixth aspect of the present invention, a method for the preparation of compound of formula 11 is provided, wherein the method includes: In an inert solvent, under a blue light, subjecting compound 10 to a photochemical reaction to obtain the compound 11;

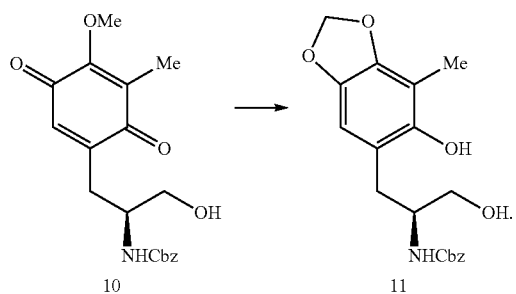 [SMILES: COC1=C(C)C(=O)C(C[C@@H](CO)NC(=O)OCc2ccccc2)=CC1=O ; Cc1c(O)c(C[C@@H](CO)NC(=O)OCc2ccccc2)cc2c1OCO2]

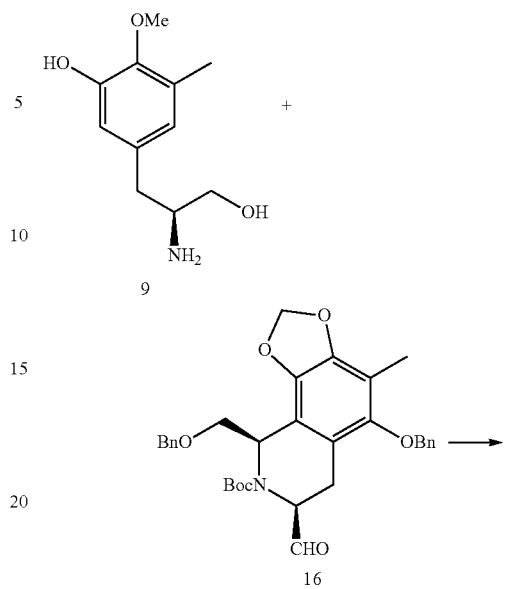

In another preferred example, the inert solvent is selected from the group consisting of Et$_2$O, MeCN, toluene, f-BuOH, THF, DMF, acetone, or the combinations thereof.

In another preferred example, the blue light is a light with a wavelength in the range of 400-500 nm.

In the seventh aspect of the present invention, a method for the preparation of compound of formula 35 is provided, wherein the method comprises:

In an inert solvent, under a blue light, subjecting compound 34 to a photochemical reaction to obtain the compound 35;

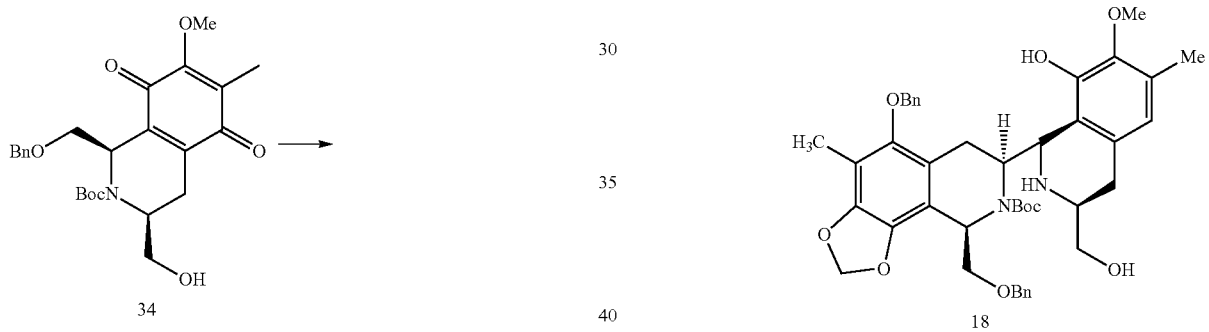

In another preferred example, the inert solvent is selected from the group consisting of Et$_2$O, MeCN, toluene, f-BuOH, THF, DMF, acetone, or the combinations thereof.

In another preferred example, the blue light is a light with a wavelength in the range of 400-500 nm.

In the eighth aspect of the present invention, a method for the preparation of compound of formula 18 is provided, wherein the method comprises:

(a) reacting compound 9 with compound 16 to obtain compound 18:

In another preferred example, in the step (a), the reaction is performed in the presence of a catalyst (preferably selected from TFA, BF$_3$.OEt$_2$, HCOOH, TsOH, AcOH, Yb(OTf)$_3$), and preferably, the catalyst is AcOH.

In another preferred example, the step (a) is carried out in the presence of 4A molecular sieve.

In another preferred example, the reaction is carried out at 40-60° C.

In another preferred example, the reaction is performed in a solvent selected from the group consisting of toluene, DCM, TFE, or the combinations thereof; and preferably, the reaction is performed in DCM:TFE=1-10:1 (preferably 3-7:1) (v:v) solvent mixture.

In another preferred example, in the step (a), the reaction is carried out at 60-80° C.

In another preferred example, the reaction is carried out in toluene:DCM:TFE=1-5:0.8-1.2:1 (v:v:v)) solvent.

In the ninth aspect of the present invention, a method for the preparation of compound 20 is provided, wherein the method comprises:

(c) subjecting compound 19 to the following reaction to obtain compound 20:

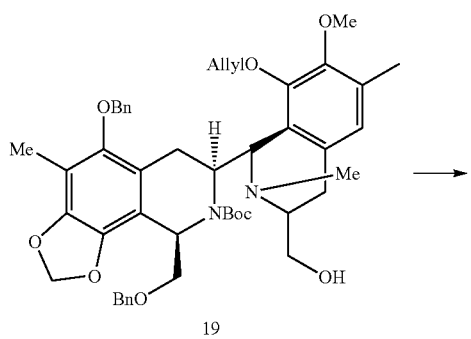

19

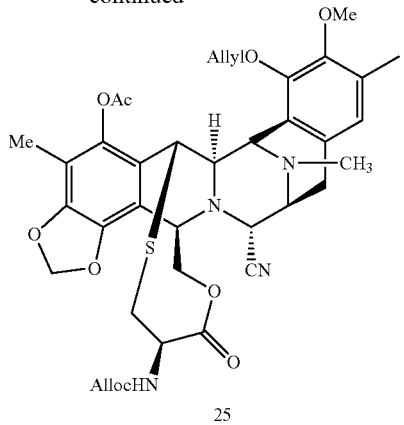

25

In another preferred example, in the step (g), the reaction comprises:

Sequentially reacting compound 24 in (1) Tf$_2$O, DMSO; (2) DIPEA, 0° C.; (3) tBuOH, room temperature; (4)

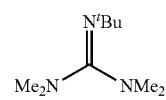

and (5) Ac$_2$O, room temperature, thereby obtaining compound 25.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

After long-term and in-depth research, the present inventors have developed a synthetic method for Trabectedin. The method uses tyrosine as the starting substrate and can complete the synthesis within 26 steps of reaction. The raw materials and reagents used are relatively easy to be obtained, and the reaction conditions are relatively mild, thus enabling large-scale preparation. The present invention is completed on this basis.

Synthesis of Trabectedin

Currently, the drug is obtained through semi-synthesis by using cyanosafracin B as a raw material, which is obtained from *Pseudomonas fluorescens* by fermentation. Even if the method is a semi-synthesis route, it still needs 22 steps of reaction and the total yield is only 1.0%. Such way for obtaining the compound makes the Trabectedin production very costly.

The present invention provides a novel synthetic route that uses tyrosine as the starting substrate and natural chiral source, and the five-membered ring is closed through a simple and efficient photocatalytic reaction. The first tetrahydroisoquinoline ring is formed by Bischler-Napieralski reaction, or the first tetrahydroisoquinoline ring is closed by Pictet-Spengler reaction, and then the five-membered ring is closed by a highly efficient photocatalytic reaction. The two fragments are connected by Pictet-Spengler reaction into a closed loop to construct the second tetrahydroisoquinoline

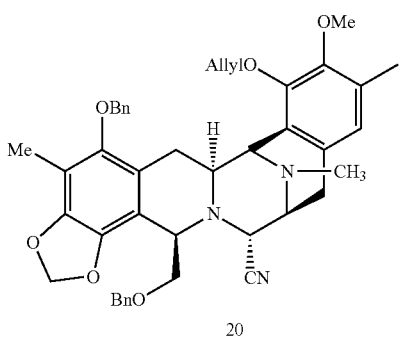

20

In another preferred example, in the step (c), the method includes: after the reaction conducted under Swern oxidation condition, the ring is closed in the presence of TFA, DCM, and TMSCN.

In the tenth aspect of the present invention, a method for the preparation of compound is provided, wherein the method comprises:

(g) subjecting compound 24 to the following reaction to obtain compound 25:

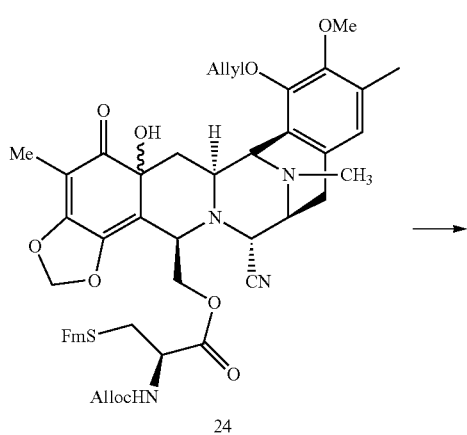

24 ring in the molecular framework. The piperazine ring in the molecular framework structure is closed by intramolecular Strecker reaction to complete the molecule construction of the five-ring skeleton. Afterwards, the product is deprotected, a cysteine side chain is connected through condensation, the ten-membered thiolactone ring is closed, and the last tetrahydroisoquinoline structure was formed by a second Pictet-Spengler reaction, thereby completing the synthesis of the molecule. This route uses a convergent synthesis strategy, starts from the readily available natural chiral source tyrosine, and completes the full synthesis of Et-743 within at minimum 26 steps. The raw materials and reagents used in the synthetic route are relatively easy to be obtained, and used reaction conditions are mild, thus enabling large-scale preparation.

Overview of Synthetic Route

According to the new route of the present invention, compounds 9 and 16 can be synthesized separately from tyrosine, and these two compounds can form key intermediates 18 through P-S reaction. Then compound 25 was obtained through multiple steps of transformation (all the above steps are new developed synthetic route). Then the compound 25 was converted into an reported high-level intermediate through deprotection, and Et-743 was synthesized using the previously reported route. As reported in the known publications, compound 8 is synthesized from L-tyrosine in 6 steps (R. Chen, D. Zhu, Z. Hu, Z. Zheng, X. Chen, *Tetrahedron: Asymmetry,* 2010, 21, 39-42.)

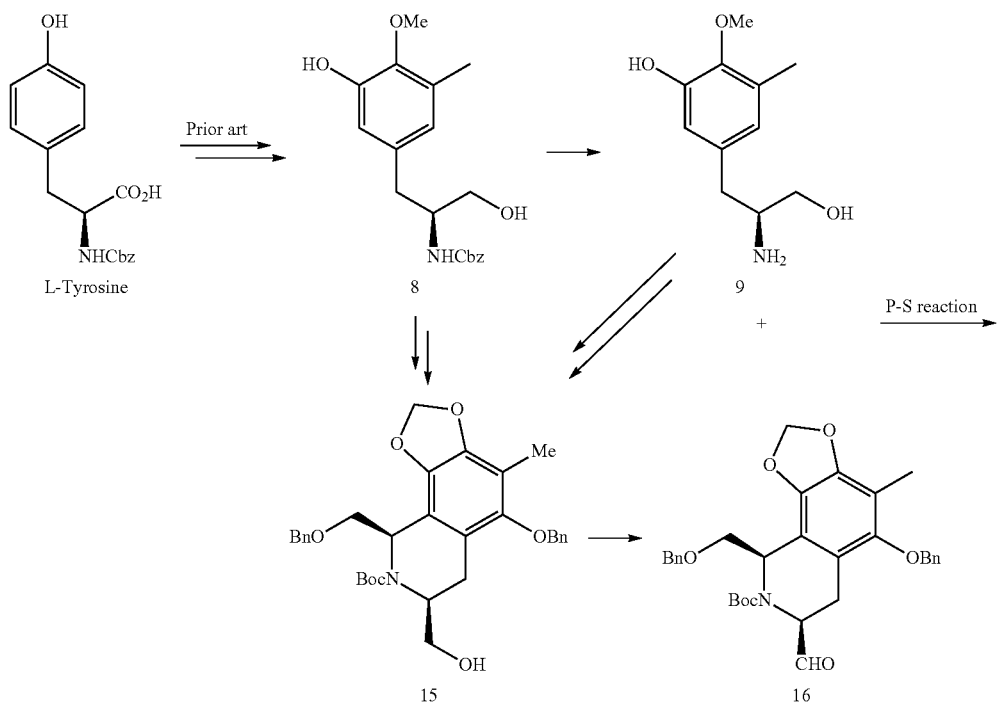

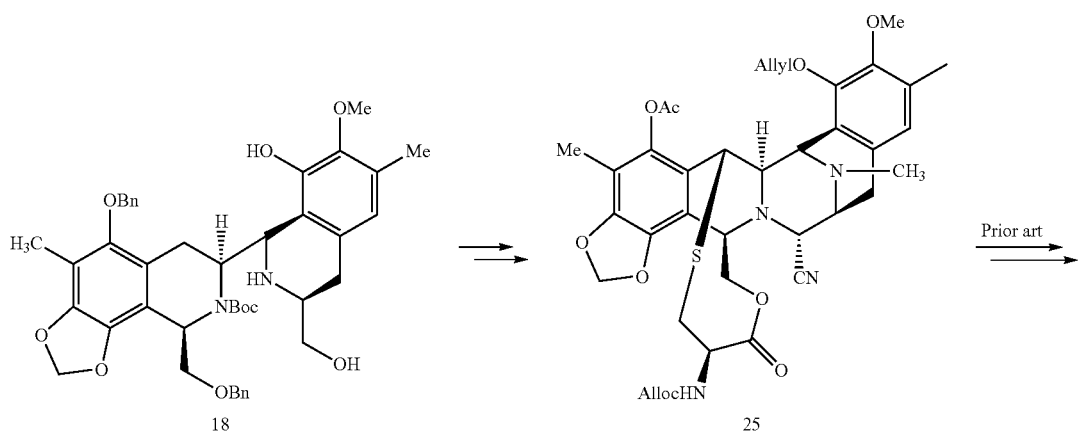

-continued
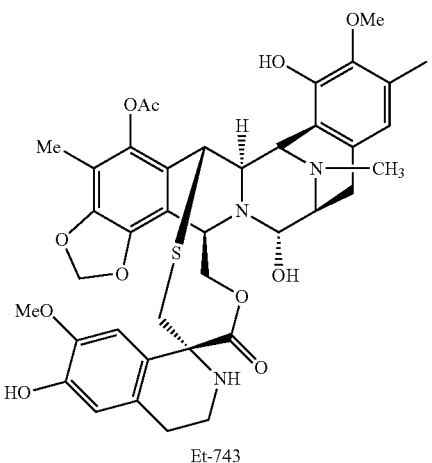
Et-743
(1) Synthesis of Compound 9
Compound 9 is obtained by deprotecting compound 8 by hydrogenation.
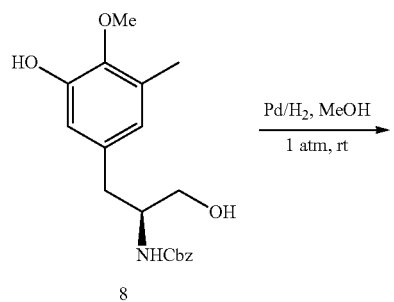
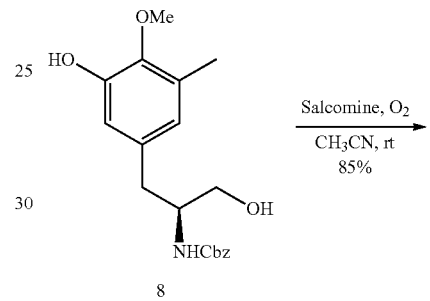
(2) Synthesis of Compound 16
Compound 16 is prepared from compound 8 through a multi-step reaction via compounds 10, 11, 12, 13, 14 and 15. Structure of each new compound is determined by $^1$H NMR, $^{13}$C NMR, MS structure, and the cis-trans structure of compound 15 is determined by Noesy.
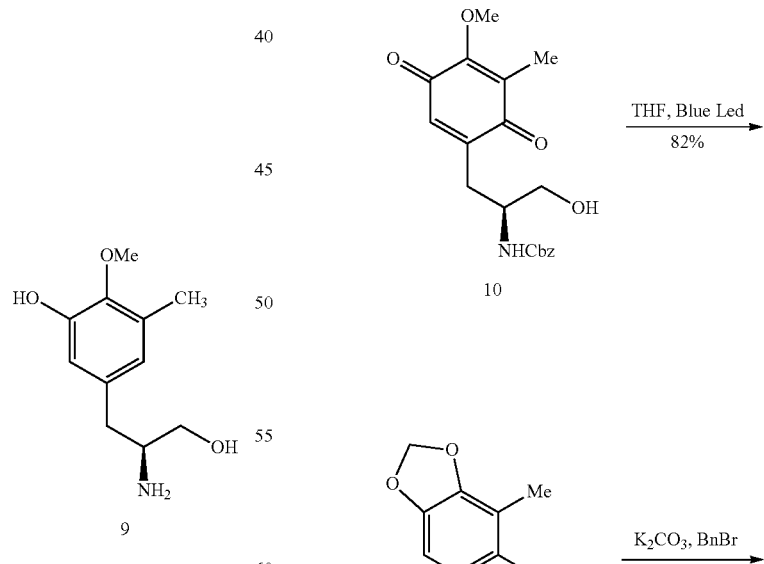

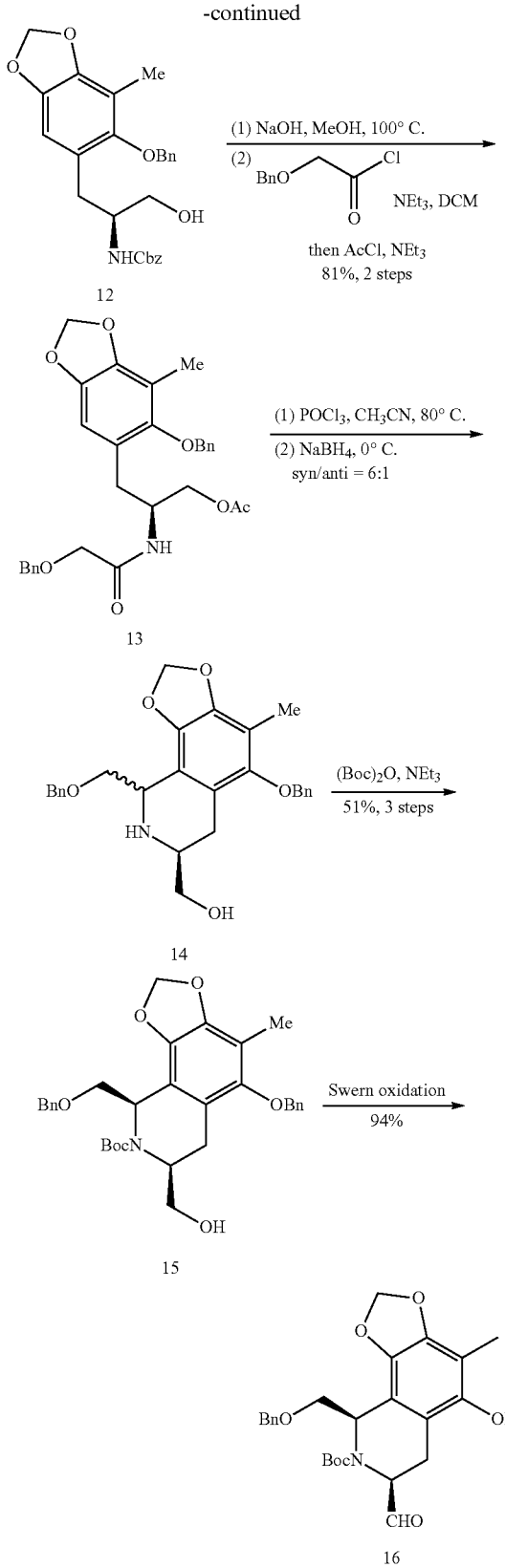

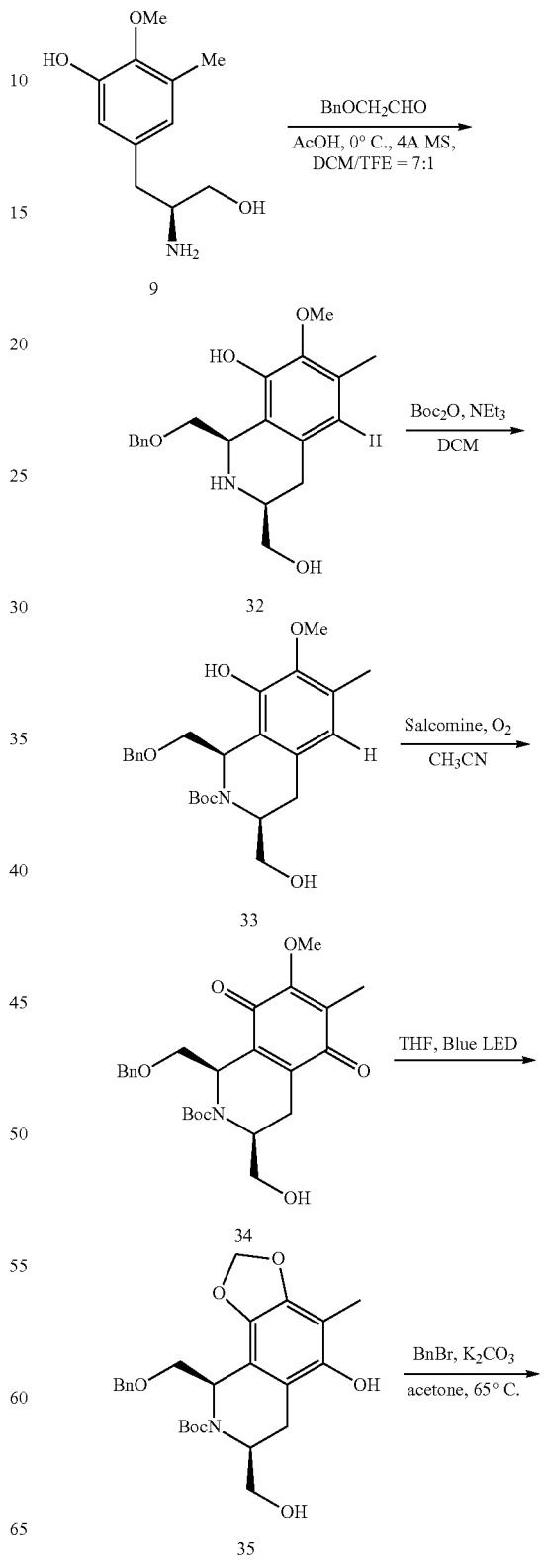

good yield and the reaction conditions are simple, thus being suitable for large-scale preparation.

Compound 16 can also be prepared according to the following route: preparing compound 15 from compound 9, and then compound 16 is prepared by compound IS:

The photocatalytic reaction from compound 10 to compound 11 is a critical and novel reaction, which can complete the conversion that normally require 3 steps in one step with

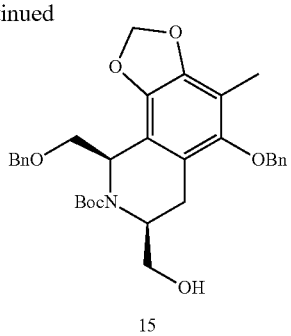

The inventors optimized the conditions for the two photoreactions, in which compound 11 is prepared from compound 10 and compound 35 is prepared from compound 34. The results are as follows:

Based on the above results, it is found that the preferred light source is blue light. The following solvents are screened: DMF, acetone, acetonitrile, t-butanol, toluene, etc., and the preferred solvent is THF.

(3) Synthesis of Compound 25

The two fragments (compounds 9 and 16) are connected through Pictet-Spengler reaction into a closed loop to construct the second tetrahydroisoquinoline ring in the molecular framework. The piperazine ring in the molecular framework structure is closed through intramolecular Strecker reaction to complete the molecule construction of the five-ring skeleton (preparation of compound 20 from compound 19). Then compound 22 is obtained through deprotection, a cysteine side chain is connected through condensation to obtain compound 24, and the ten-membered thiolactone ring is closed to obtain compound 25:

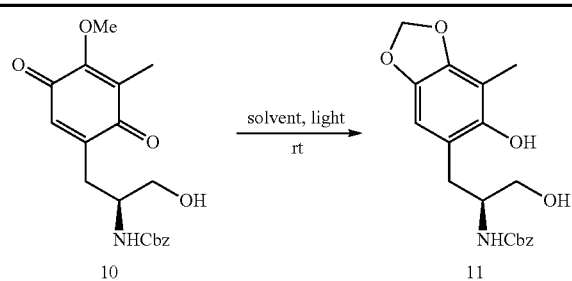

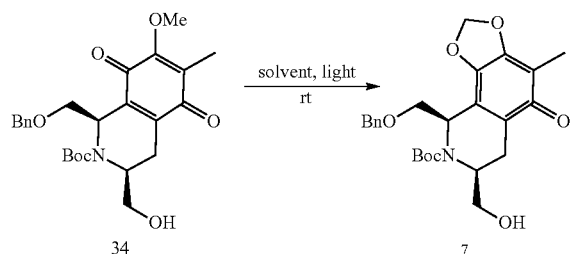

| Entry | Condition | Yield of Compound 11 (%) [b] | Yield of Compound 35 (%) [b] |
|---|---|---|---|
| 1 | Daylight, Et$_2$O | 44 | 41 |
| 2 | White light, Et$_2$O | 41 | 42 |
| 3 | Blue light, Et$_2$O | 51 | 48 |
| 4 | Medium pressure Hg lamp | 38 | 31 |
| 5 | Uv (365 nm), Et$_2$O | 44 | 39 |
| 6 | Blue light, THF | 83 | 75 |
| 7 | Blue light, t-BuOH | 19 | 22 |
| 8 | Blue light, MeCN | none | none |
| 9 | Blue light, toluene | 40 | 41 |
| 10 | Blue light, DMF | 3 | trace |
| 11 | Blue light, acetone | 2 | 7 |

[a] Reaction conditions: Compound 10 or 34 (0.5 mmol), solvent (5 mL), RT, 2 h.
[b] Yield is calculated according to $^1$H NMR (using CH$_2$Br$_2$ as internal standard) analysis.

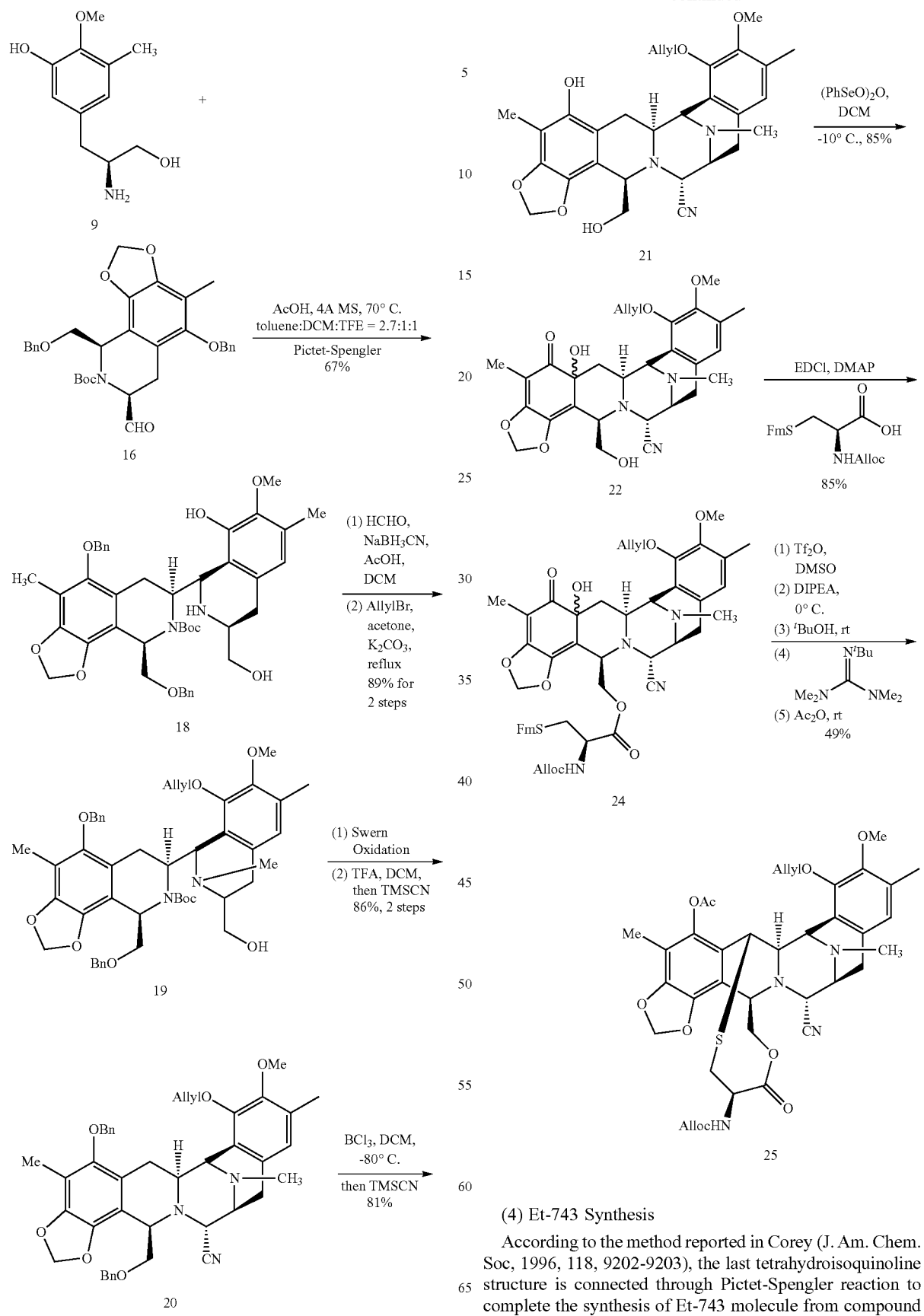
(4) Et-743 Synthesis
According to the method reported in Corey (J. Am. Chem. Soc, 1996, 118, 9202-9203), the last tetrahydroisoquinoline structure is connected through Pictet-Spengler reaction to complete the synthesis of Et-743 molecule from compound 25.

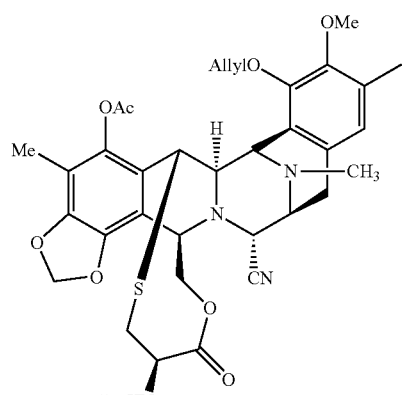
25
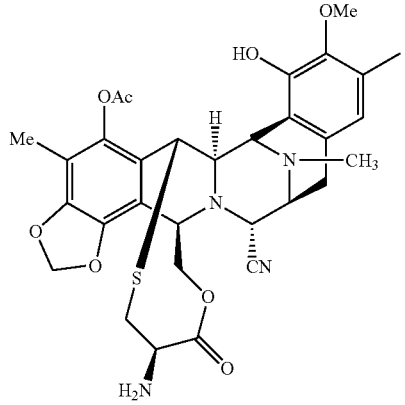
26
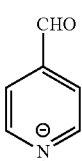
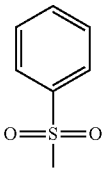
then DBU, then
(COOH)$_2$
57%
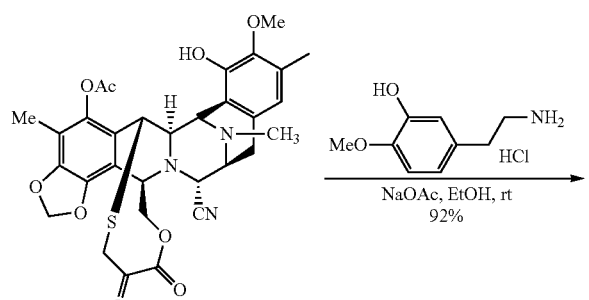
28
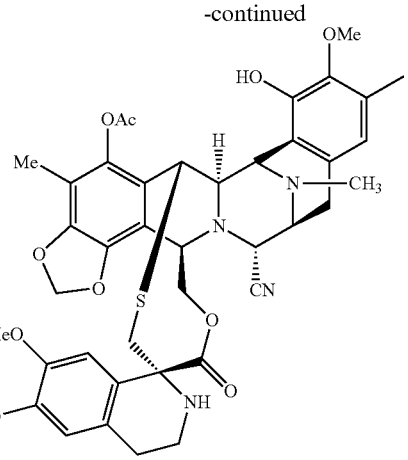
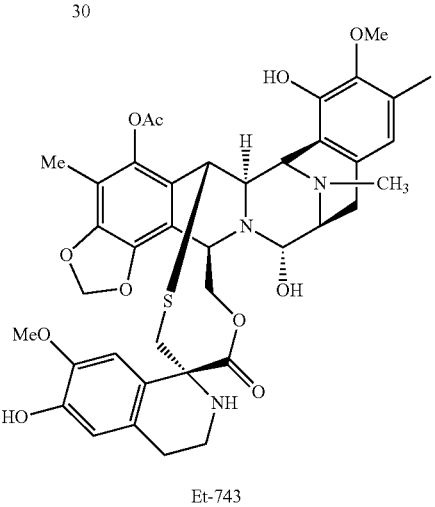
Et-743
Et-743 Intermediate Compound
In the method of the present invention, a series of intermediate compounds that can be used to prepare Et-743 are obtained:
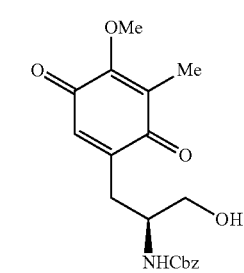
10
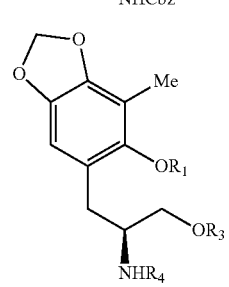
I -continued
I-1
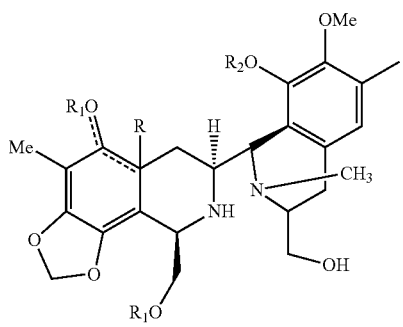
I-2
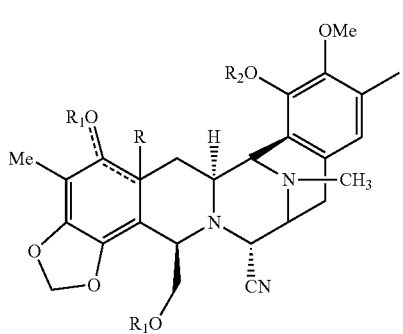
I-3
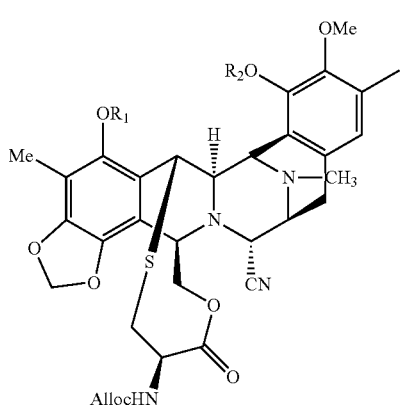
34
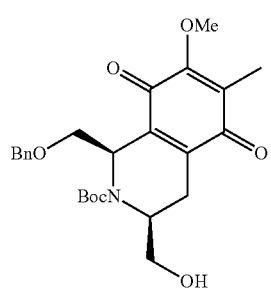
35
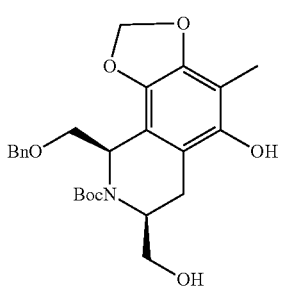
wherein,
R₁ is selected from the group consisting of H, Bn-, allyl and
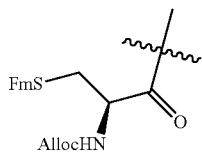
R₂ is selected from the group consisting of H, Bn- and allyl;
R₃ is selected from the group consisting of H and Ac;
R₄ is selected from the group consisting of Cbz and
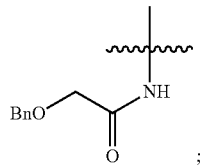 [SMILES: *NC(=O)COCc1ccccc1]
R is selected from the group consisting of H and OH.
The preferred intermediate structures are as follows:
10
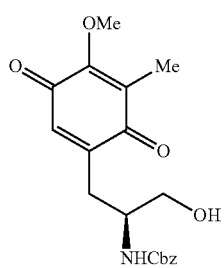
11
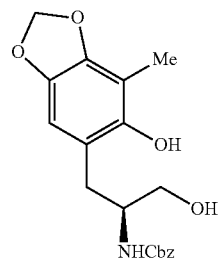
12
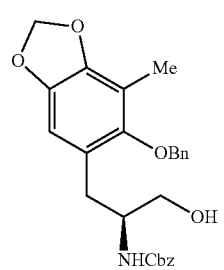

13
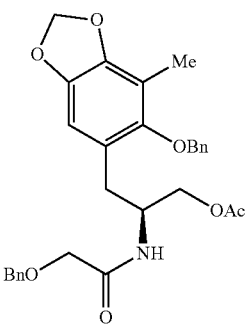
14
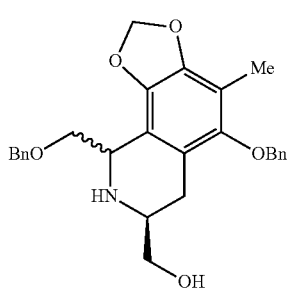
15
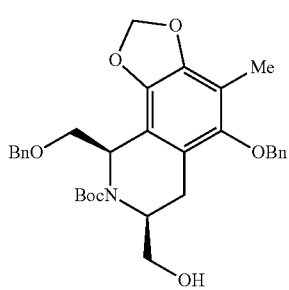
16
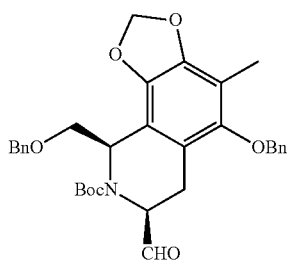
18
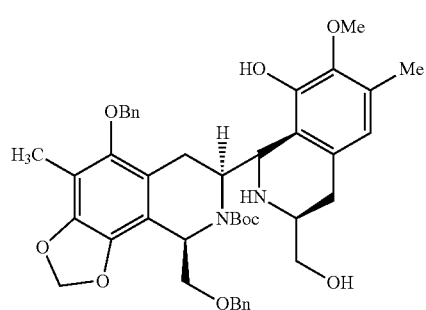
19
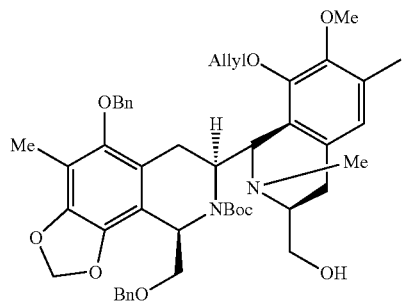
20
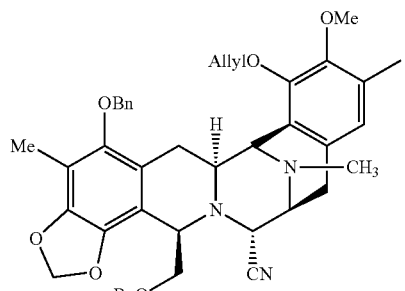
21
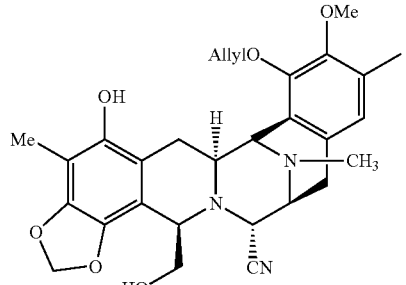
22
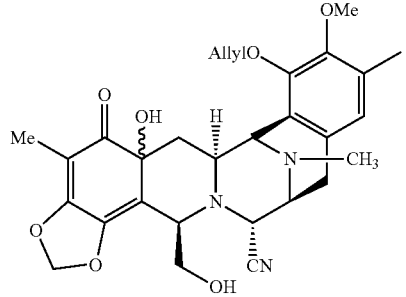
24
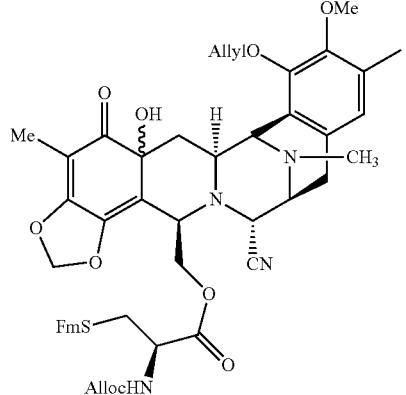

-continued

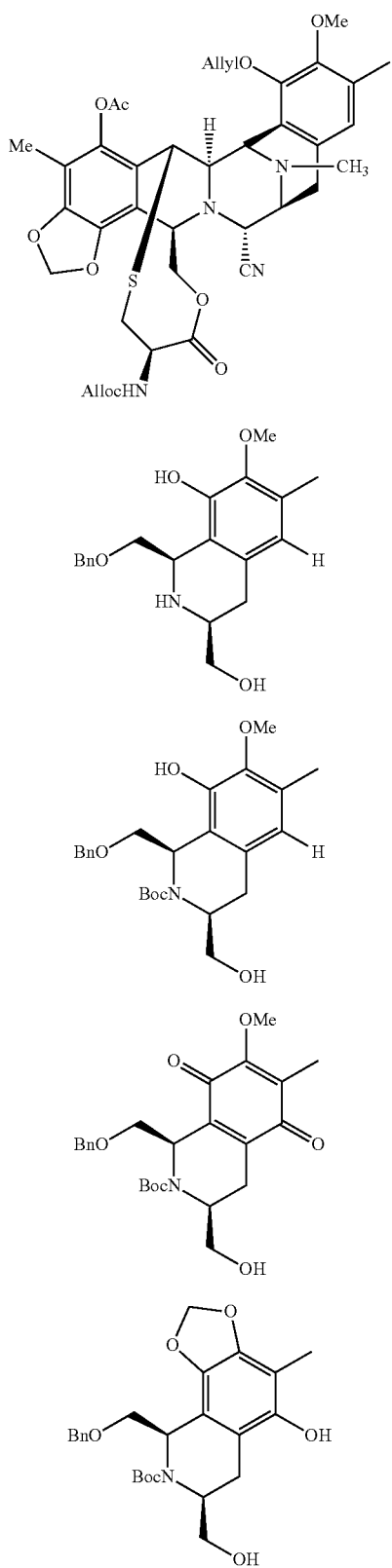

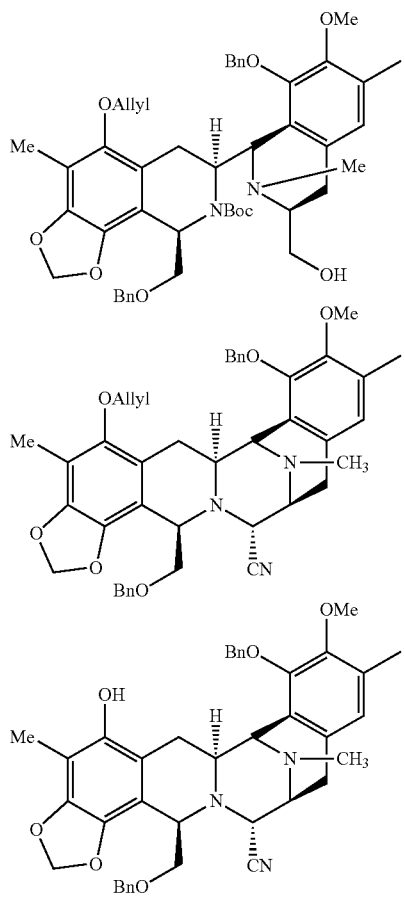

Compared with the prior art, the main advantages of the present invention includes:

(1) The synthetic route of the present invention is inspired by the biogenic pathway of Et 743, the readily available natural chiral source tyrosine is used as the only starting substrate, the important five-ring skeleton intermediate is quickly and efficiently constructed, and the raw materials and reagents used in the synthetic route are relatively easy to be obtained and of low cost;

(2) The reaction conditions of each step of the synthesis method of the present invention are relatively mild, and the photocatalytic ring-closure reaction is environmentally friendly and highly effective, thus being suitable for large-scale preparation;

(3) The synthesis route of the method of the present invention is short, and the synthesis of Et-743 can be simply completed in 26 steps.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

As reported in the known publications, compound 8 is synthesised from L-tyrosine in 6 steps (R. Chen, D. Zhu, Z. Hu, Z. Zheng, X. Chen, *Tetrahedron: Asymmetry*, 2010, 21, 39-42.)

Among them, compound 18 can also be synthesized using the following several intermediates with different protecting groups.

Example 1 Synthesis of Compound 9

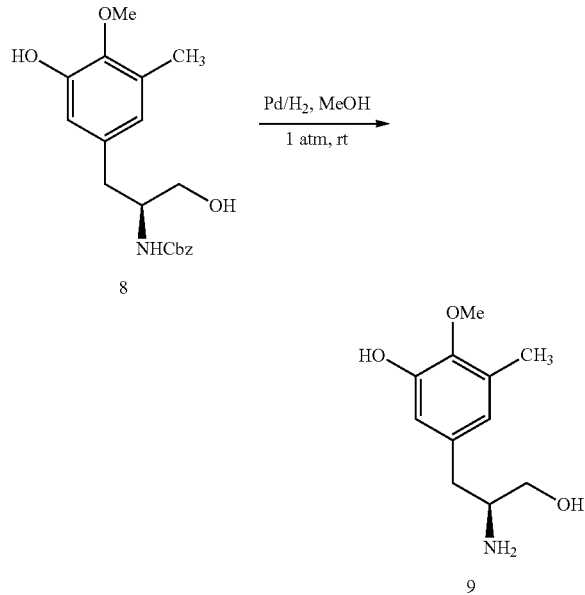

Compound 8 (6.7 g, 19.4 mmol) was dissolved in methanol, and 0.67 g of 10% Pd/C was weighed in a 250 ml flask. Methanol was injected under the protection of argon into the system, and the atmosphere was exchanged with hydrogen for 3 times, the reaction was performed at room temperature for 6 hours at 1 atm. The point on the TLC plate (DCM: MeOH=10:1) showed that the raw material was consumed. Pd/C was filtered off with celite, and the solvent was removed under reduced pressure to obtain 4.0 g of compound 9, yield 98%.

Compound 9: $^1$H NMR (400 MHz, CD$_3$OD) δ 6.60 (d, J=1.9 Hz, 1H), 6.55 (d. J=1.5 Hz, 1H), 3.73 (s, 3H), 3.63 (dd, J=11.3, 3.9 Hz, 1H), 3.45 (dd, J=11.2, 6.6 Hz, 1H), 3.22 (td, J=11.0, 6.9 Hz, 1H), 2.72 (dd, J=13.6, 7.3 Hz, 1H), 2.62 (dd, J=13.2, 7.5 Hz, 1H), 2.22 (s, 3H).

$^{13}$C NMR (100 MHz, CD$_3$OD) δ 151.21, 146.30, 134.10, 132.93, 123.44, 116.04, 63.73, 60.41, 55.65, 37.81, 15.95.

HRMS (ESI): calcd. for C$_{11}$H$_{18}$NO$_3$ [M+H]$^+$ 212.1287; found 212.1291.

Example 2 Synthesis of Compound 10

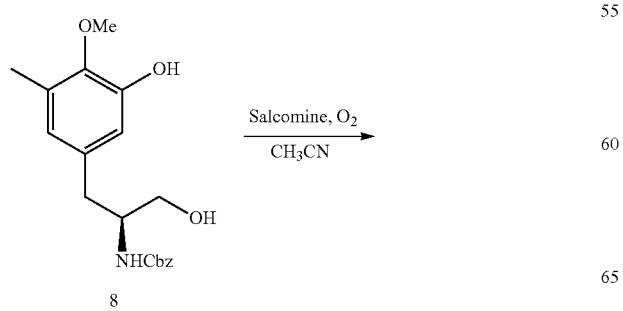

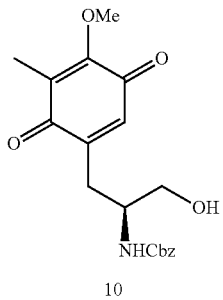

The atmosphere of raw material 8 (6.0 g, 17.38 mmol) was exchanged with oxygen, and the solvent acetonitrile was added under the oxygen atmosphere to dissolve raw material 8. The catalyst salcomine (0.56 g, 1.74 mmol) was added, and the reaction was stirred under an oxygen atmosphere at room temperature. The mixture was black, and the reaction was completed after 2 h. The black catalyst was removed by filtration through celite, and the solvent was removed under reduced pressure, and purified by flash column chromatography (EA:PE=1:2) to obtain 5.6 g of bright yellow solid 10, yield 91%.

Compound 10: $^1$H NMR (400 MHz, CDCl$_3$) δ 7.35-7.25 (m, 5H), 6.48 (s, 1H), 5.45-5.43 (d, J=8.68 Hz, 1H), 5.07-4.97 (m, 2H), 4.00 (s, 3H), 3.90-3.80 (m, 1H), 3.67-3.51 (m, 2H), 3.11-3.00 (m, 1H), 2.77-2.65 (m, 1H), 2.60-2.47 (m, 1H), 1.93 (s, 3H)

$^{13}$C NMR (100 MHz, CDCl$_3$) δ 188.7, 188.3, 156.4, 155.6, 145.3, 136.3, 132.8, 128.7, 128.6, 128.2, 128.0, 66.8, 64.2, 60.9, 52.6, 31.3, 9.0

HRMS (ESI): calcd. for C$_{19}$H$_{22}$NO$_6$ [M+H]$^+$ 360.1447; found 360.1451.

Example 3 Synthesis of Compound 11

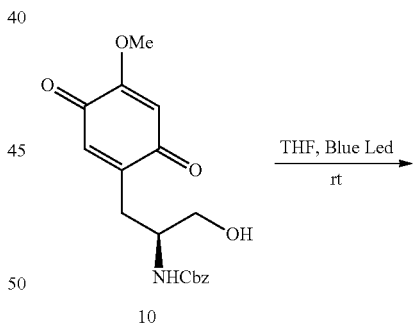

The yellow compound 10 (8.0 g, 22.3 mmol) was dissolved in 220 mL of anhydrous THF solvent under the protection of argon, and stirred at room temperature under blue light irradiation. The reaction was completed after 8 h. The THF solvent was removed under reduced pressure. Flash column chromatography purification (EA:PE=1:2) was performed to afford 6.6 g of white solid product 11 in 82% yield.

Compound 11: $^1$H NMR (400 MHz, CDCl$_3$) δ 7.43-7.30 (m, 5H), 6.41 (s, 1H), 5.86 (s, 2H), 5.54-5.52 (d, J=7.24 Hz, 1H), 5.11 (s, 2H), 3.79-3.31 (m, 4H), 2.90-2.67 (m, 2H), 2.13 (s, 3H)

$^{13}$C NMR (100 MHz, CDCl$_3$) δ 157.1, 148.3, 145.7, 140.3, 136.1, 128.6, 128.3, 128.2, 114.4, 108.8, 107.0, 100.7, 67.2, 62.4, 53.7, 31.9, 9.2

HRMS (ESI): calcd. for C$_{19}$H$_{22}$NO$_6$ [M+H]$^+$ 360.1447; found 360.1452.

Example 4 Synthesis of Compound 12

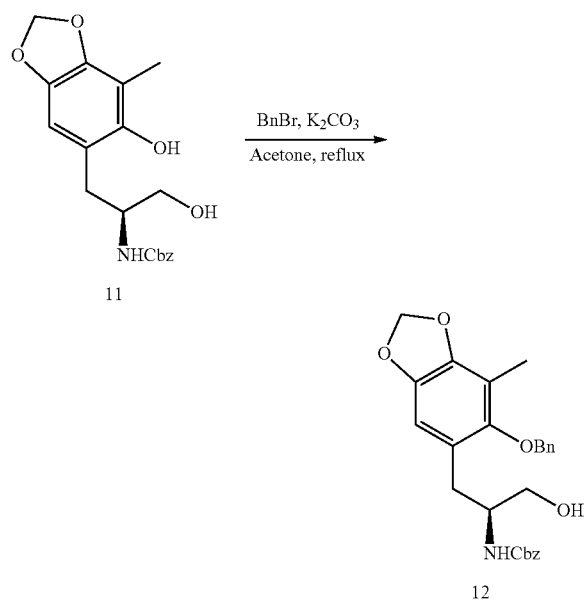

Example 5 Synthesis of Compound 13

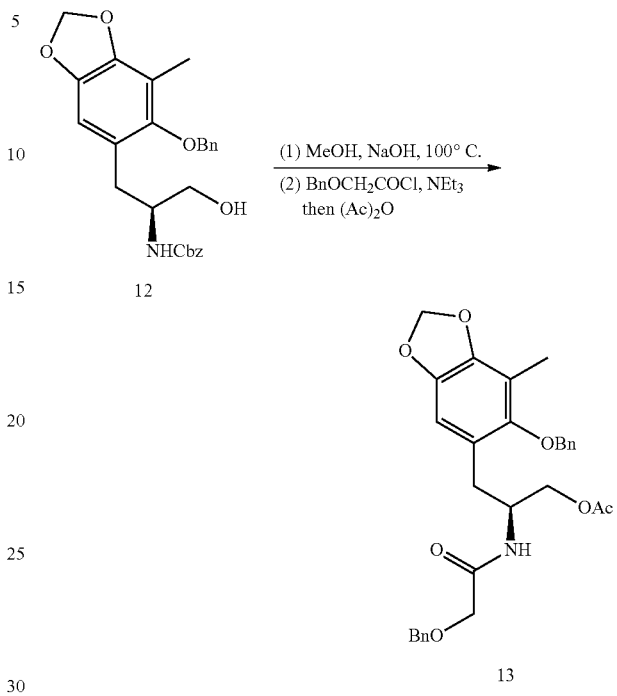

The compound 11 (6.6 g, 18.38 mmol) was dissolved in 180 mL of acetone, K$_2$CO$_3$ (5.07 g, 36.77 mmol) and BnBr (3.27 mL, 27.57 mmol) were added, and the reaction was refluxed at 65° C. for two hours. The reaction was completed as determined by TLC, and acetone was distilled off under reduced pressure. Water was added, and extracted three times with ethyl acetate, the combined organic phases was dried over anhydrous sodium sulfate, the solvent was distilled off under reduced pressure, and flash column chromatography (EA:PE=3:1) purification was performed to afford 7.67 g of product. Yield 93%.

Compound 12: $^1$H NMR (400 MHz, CDCl$_3$) δ 7.46-7.29 (m, 10H), 6.57 (s, 1H), 5.94 (s, 2H), 5.37 (d, J=7.6 Hz, 1H), 5.08 (s, 2H), 4.78 (dd, J=34.5, 11.0 Hz, 2H), 3.80-3.68 (m, 1H), 3.43 (d, J=2.7 Hz, 2H), 2.75 (d, J=7.3 Hz, 2H), 2.22 (s, 3H).

$^{13}$C NMR (101 MHz, CDCl$_3$) δ 156.44, 150.12, 145.82, 143.67, 136.59, 136.38, 128.82, 128.58, 128.51, 128.05, 128.03, 127.96, 122.74, 113.45, 107.28, 101.26, 76.07, 66.62, 63.31, 54.23, 31.56, 9.80.

HRMS (ESI): calcd. for C$_{26}$H$_{27}$NO$_6$ [M+H]$^+$ 450.1917; found 450.1918.

The compound 12 (2.54 g, 5.66 mmol) was dissolved in 50 mL of methanol, and 30 mL of 2M NaOH aqueous solution was added. The cloudy mixture was heated to 100° C. to reflux, and the system gradually turned to clear. The reaction was completed after 2 hours, the methanol was distilled off under reduced pressure, and the resulting system was extracted with ethyl acetate. The combined organic phases was dried over anhydrous sodium sulfate, and the solvent was distilled off under reduced pressure. The obtained crude product was dissolved in 50 mL of anhydrous dichloromethane, and NEt$_3$ was added (3.13 mL, 22.64 mmol). Benzyloxyacetyl chloride (0.8 mL, 5.1 mmol) dissolved in 10 mL of dichloromethane was slowly added dropwise at 0° C. in 15 minutes. The reaction was completed and (Ac)$_2$O (1.07 mL, 11.32 mmol) was added and reacted for another 2 hours at room temperature. After the reaction was completed, the mixture was extracted with dichloromethane for three times, and the combined organic phases was distilled to remove the solvent under reduced pressure. Flash column chromatography (EA:PE=1:3) purification was performed to afford 2.3 g of white solid compound 13, two-step yield was 81%.

Compound 13: $^1$H NMR (400 MHz, CDCl$_3$) δ 7.46-7.29 (m, 8H), 7.27-7.23 (m, 2H), 6.95 (d, J=8.2 Hz, 1H), 6.52 (s, 1H), 5.93 (d, J=0.6 Hz, 2H), 4.83-4.68 (m, 2H), 4.46 (d, J=6.7 Hz, 2H), 4.40-4.28 (m, 1H), 4.13-3.99 (m, 2H), 3.87 (d, J=13.8 Hz, 2H), 2.17 (s, 3H), 1.94 (s, 3H).

$^{13}$C NMR (100 MHz, CDCl$_3$) δ 170.8, 169.5, 150.5, 145.8, 143.3, 137.2, 137.0, 128.58, 128.55, 127.75, 127.69, 122.35, 113.6, 107.0, 101.2, 75.4, 73.4, 69.4, 65.1, 49.2, 31.8, 20.7, 9.8.

HRMS (ESI): calcd. for C$_{29}$H$_{32}$NO$_7$ [M+H]$^+$ 506.2179; found 506.2183.

51
Example 6 Synthesis of Compound 14

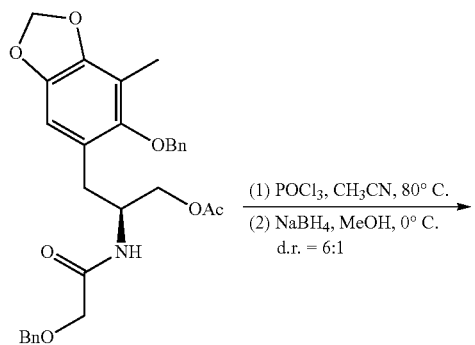

13

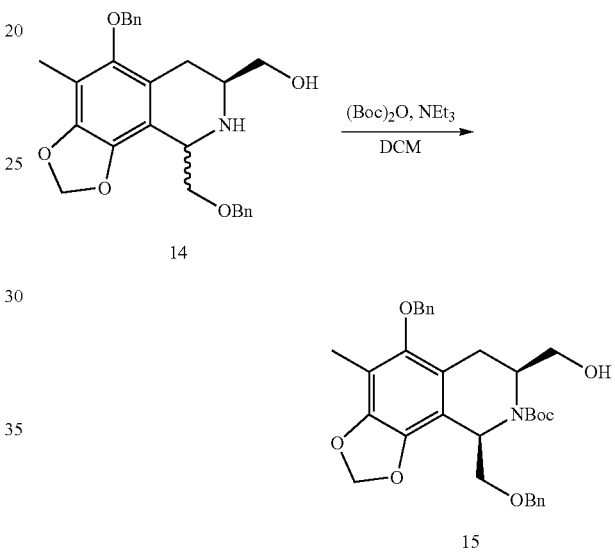

Under argon protection, the compound 13 (8.5 g, 16.83 mmol) was dissolved in 170 mL of anhydrous acetonitrile. POCl$_3$ (3.14 mL, 33.66 mmol) was added and warmed to 80° C. to reflux for 3 hours. After the reaction was completed, saturated NaHCO$_3$ solution was added until the reaction solution was neutral, and extracted with ethyl acetate for three times. The organic phases were combined, washed with saturated brine, dried over anhydrous sodium sulfate. The solvent was distilled off under reduced pressure, and the residue was dried. The obtained crude product was dissolved in 150 mL of anhydrous methanol, and NaBH$_4$ (3.18 g, 84.15 mmol) was added in portions at 0° C. and reacted for 4 hours. After the reaction was completed, the solvent was distilled off under reduced pressure, and the obtained crude product was used in the next reaction.

Compound 14a: $^1$H NMR (400 MHz, CDCl$_3$) δ 7.46-7.26 (m, 10H), 5.83 (s, 1H), 4.81 (d, J=11.2 Hz, 1H), 4.69 (d, J=11.2 Hz, 1H), 4.55 (q, J=12.0 Hz, 1H), 4.28 (d, J=4.5 Hz, 1H), 4.12 (dd, J=9.3, 2.9 Hz, 1H), 3.85 (dd, J=9.3, 6.6 Hz, 1H), 3.78 (dd, J=10.9, 3.7 Hz, 1H), 3.53 (dd, J=10.9, 7.5 Hz, 1H), 2.97-2.85 (m, 1H), 2.81 (dd, J=15.9, 2.8 Hz, 1H), 2.32 (dd, J=15.5, 11.4 Hz, 1H), 2.15 (s, 1H).

$^{13}$C NMR (100 MHz, CDCl$_3$) δ 149.65, 144.39, 139.49, 138.31, 137.37, 128.56, 128.31, 128.09, 127.85, 127.77, 127.62, 121.95, 115.17, 112.22, 100.70, 74.58, 73.27, 71.53, 65.94, 54.42, 54.09, 26.70, 9.46.

HRMS (ESI): calcd. for C$_{27}$H$_{30}$NO$_5$ [M+H]$^+$ 448.2124; found 448.2120.

52

Compound 14b: $^1$H NMR (400 MHz, CDCl$_3$) δ 7.44-7.22 (m, 10H), 5.83 (dd, J=10.4, 1.4 Hz, 2H), 4.77 (d, J=11.2 Hz, 1H), 4.66 (dt, J=11.1, 5.7 Hz, 2H), 4.52-4.44 (m, 2H), 3.79 (ddd, J=13.7, 10.8, 2.9 Hz, 2H), 3.61 (dd, J=19.2, 9.7 Hz, 2H), 3.22-3.12 (m, 1H), 2.74 (dd, J=16.6, 3.8 Hz, 1H), 2.53 (dd, J=16.6, 11.1 Hz, 1H), 2.12 (s, 3H).

$^{13}$C NMR (100 MHz, CDCl$_3$) δ 149.60, 144.45, 139.57, 137.89, 137.26, 128.55, 128.43, 128.11, 127.93, 127.82, 127.78, 119.97, 112.75, 112.30, 101.23, 74.42, 73.11, 68.32, 64.73, 51.03, 49.57, 25.17, 9.44

HRMS (ESI): calcd. for C$_{27}$H$_{30}$NO$_5$ [M+H]$^+$ 448.2124; found 448.2120.

Example 7 Synthesis of Compound 15

The crude compound 14 obtained in the previous step was dissolved in 150 dichloromethane, and (Boc)$_2$O (11.02 g, 50.49 mmol) and NEt$_3$ (6.98 mL, 50.49 mmol) were added. The reaction was stirred at room temperature for 4 hours. After the reaction was completed, 100 mL of water was added, extracted with dichloromethane for three times. The combined organic phases were washed with saturated brine, dried over anhydrous sodium sulfate, filtered, the solvent was distilled off under reduced pressure, and flash column chromatography (EA:PE=6:1) purification was performed to afford 4.69 g of colorless oily compound 15 with a yield of 51% in three steps.

Compound 15: $[α]_D^{24.6}$=1.60 (c=1.0, CHCl$_3$) $^1$H NMR (400 MHz, CDCl$_3$) δ 7.45-7.25 (m, 10H), 5.86 (t, J=5.4 Hz, 2H), 5.77-5.42 (m, 1H), 4.73 (s, 2H), 4.71-4.57 (m, 1H), 4.52 (d, J=11.8 Hz, 1H), 4.28 (d, J=37.5 Hz, 1H), 3.93-3.68 (m, 3H), 3.57-3.19 (m, 2H), 2.99-2.69 (m, 2H), 2.18 (s, 3H), 1.46 (s, 9H).

Compound 15: $^{13}$C NMR (100 MHz, CDCl$_3$) δ 155.84, 149.26, 144.52, 139.33, 137.68, 137.12, 128.60, 128.34, 128.23, 128.02, 127.76, 127.74, 80.53, 75.22, 72.89, 70.58, 64.36, 52.52, 49.88, 48.51, 28.42, 23.44, 9.50.

HRMS (ESI): calcd. for C$_{32}$H$_{37}$NO$_7$Na [M+Na]$^+$ 570.2468; found 570.2472.

Example 8 Synthesis of Compound 16

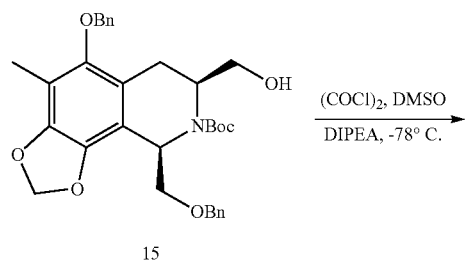

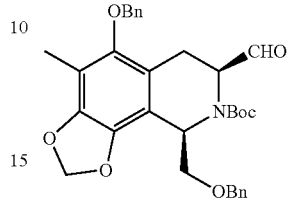

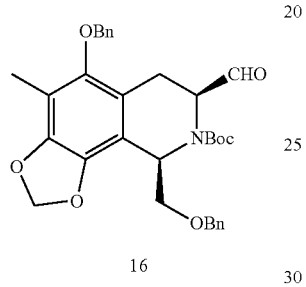

(COCl)$_2$ (0.9 mL, 10.97 mmol) was dissolved in 2 mL of anhydrous dichloromethane, and DMSO (1.56 mL, 21.94 mmol) dissolved in 2 mL of dichloromethane was slowly added dropwise at −78° C. under the protection of argon. The reaction was kept at this temperature for 30 min. then compound 15 (1.5 g, 2.74 mmol) was dissolved in 26 mL of dichloromethane, and slowly added dropwise to the system. The reaction was kept at −78° C. for another 1 hour, and afterwards, DIPEA (4.77 mL, 27.42 mmol) was added, and reacted at −78° C. for 30 min. After the reaction was completed, 10 mL of saturated ammonium chloride solution was added and extracted for three times with dichloromethane. The combined organic phases was dried with anhydrous sodium sulfate, filtered, the solvent was distilled off under reduced pressure, and flash column chromatography (EA:PE=1:5) purification was performed to obtain 1.43 g compound 16, yield 95%.

Compound 16: $^1$H NMR (400 MHz, CDCl$_3$) δ 9.46 (d, J=1.6 Hz, 0.44H), 9.41 (d, J=2.7 Hz, 0.59H), 7.45-7.14 (m, 10H), 5.88 (d, J=10.3 Hz, 2H), 5.52 (t, J=4.6 Hz, 0.52H), 5.28 (t, J=4.7 Hz, 0.45H), 4.80-4.68 (m, 2H), 4.56-4.43 (m, 2H), 4.26 (t, J=6.8 Hz, 0.38H), 4.01-3.91 (m, 0.52H), 3.84-3.59 (m, 2H), 3.04-2.67 (m, 2H), 2.18 (s, 3H), 1.48 (s, 4H), 1.43 (s, 5H).

$^{13}$C NMR (101 MHz, CDCl$_3$) δ 200.30, 199.82, 155.62, 154.78, 149.10, 148.73, 145.00, 144.85, 139.54, 139.35, 138.13, 137.93, 137.09, 136.90, 128.61, 128.26, 128.18, 127.59, 118.59, 118.30, 114.50, 113.88, 112.95, 112.79, 101.37, 101.26, 81.87, 81.49, 75.64, 75.56, 72.96, 72.30, 71.99, 60.66, 59.62, 50.34, 49.48, 28.34, 28.25, 22.16, 21.81, 9.52.

HRMS (ESI): calcd. for C$_{32}$H$_{35}$NO$_7$Na [M+Na]$^+$ 568.2311; found 568.2310.

Example 9 Synthesis of Compound 18

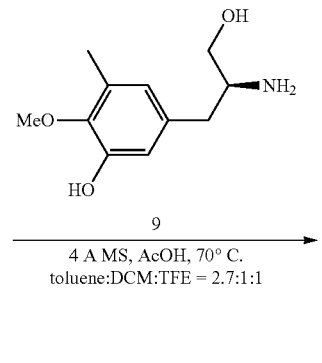

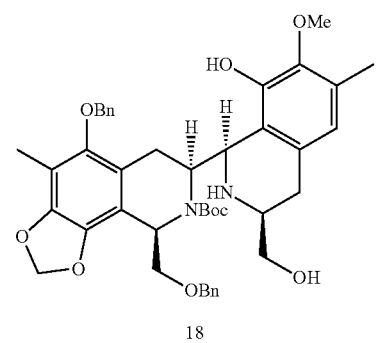

Under the protection of argon, compound 16 (3.92 g, 7.19 mmol) and compound 9 (2.28 g, 10.79 mmol), 4A molecular sieve (3.9 g) were mixed and dissolved in 40 mL/15 mL/15 mL=toluene:DCM:TFE solvent mixture. AcOH (2.06 mL, 35.96 mmol) was added and the reaction was performed overnight at 70° C. After the reaction was completed, the molecular sieve was removed by filtration through diatomaceous earth. The solvent was distilled off under reduced pressure, and flash column chromatography (EA:PE=1:2) purification was performed to afford 3.58 g of compound 18, yield 67%.

Compound 18: [α]$_D^{24.6}$=−31.50 (c=1.0, CHCl$_3$) $^1$H NMR (400 MHz, CDCl$_3$) δ 7.35-7.19 (m, 8H), 7.05 (d, J=6.4 Hz, 2H), 6.44 (s, 1H), 5.99 (s, 0.48H), 5.85 (s, 2H), 5.64 (s, 0.52H), 5.24 (s, 1H), 5.04 (s, 1H), 4.81-4.29 (m, 6H), 4.01 (d, J=49.6 Hz, 1H), 3.67 (d, J=7.0 Hz, 3H), 3.57-3.35 (m, 3H), 3.10-2.92 (m, 1.52H), 2.72-2.57 (m, 1.42H), 2.50-2.32 (m, 2H), 2.26 (s, 3H), 2.16 (s, 13H), 1.53 (s, 9H).

$^{13}$C NMR (100 MHz, CDCl$_3$) δ 177.04, 156.82, 148.77, 148.58, 146.83, 146.17, 144.36, 143.58, 139.24, 138.16, 137.71, 136.67, 132.61, 131.94, 128.54, 128.36, 122.23, 121.54, 120.99, 119.38, 115.03, 114.74, 112.76, 112.46, 101.35, 81.28, 80.77, 75.94, 75.61, 72.14, 71.78, 66.66, 66.19, 60.46, 60.23, 57.67, 55.28, 54.73, 53.88, 53.55, 52.84, 49.91, 48.65, 32.84, 22.57, 20.96, 20.00, 15.86, 9.40.

HRMS (ESI): calcd. for C$_{43}$H$_{50}$N$_2$O$_9$ [M+H]$^+$ 739.3595; found 739.3599.

For the above reaction, the inventors conducted conditional screening on the solvent system and the acid, and the screening results are as follows:

Screening for acid and reaction temperature:

| Entry | Solvent | Acid (1.5 eq) | T (° C.) | Result |
| --- | --- | --- | --- | --- |
| 1 | DCM: TFE = 7: 1 | TFA | rt-30° C. | Boc deprotected |
| 2 | DCM: TFE = 7: 1 | BF$_3$•OEt$_2$ | rt-30° C. | Boc deprotected |
| 3 | DCM: TFE = 7: 1 | HCOOH | 0° C.-rt | Complex |
| 4 | DCM: TFE = 7: 1 | TsOH | 0° C.-rt | Boc deprotected |
| 5 | DCM: TFE = 7: 1 | AcOH | 0° C. | none |
| 6 | DCM: TFE = 7: 1 | AcOH | 25° C. | trace |
| 7 | DCM: TFE = 7: 1 | AcOH | 50° C. | 16% |
| 8 | DCM: TFE = 7: 1 | AcOH | 60° C. | 15% |
| 9 | DCM: TFE = 7: 1 | Yb(OTf)$_3$ | rt-50° C. | trace |

The optimal condition is AcOH, 50° C.

Screening for reaction solvent and acid equivalents:

| Entry | Solvent | Acid (1.5 eq) | T (° C.) | Result |
| --- | --- | --- | --- | --- |
| 1 | 1,4-dioxane | AcOH | 50° C. | trace |
| 2 | THF | AcOH | 50° C. | trace |
| 3 | CH$_3$CN | AcOH | 50° C. | trace |
| 4 | DCM/TFE = 5:1 | AcOH | 50° C. | 28.2% |
| 5 | DCM/TFE = 3:1 | AcOH | 50° C. | trace |
| 6 | DCM/TFE = 1:1 | AcOH | 50° C. | trace |
| 7 | DCM/TFE = 1:2 | AcOH | 50° C. | trace |
| 8 | DCM/TFE = 5:1 | AcOH (3 eq) | 50° C. | 61% |

The optimal conditions were: the reaction solvent being DCM/TFE=5:1, the AcOH equivalent being 3 equivalents, and the reaction temperature being 50° C.

Example 10 Synthesis of Compound 19

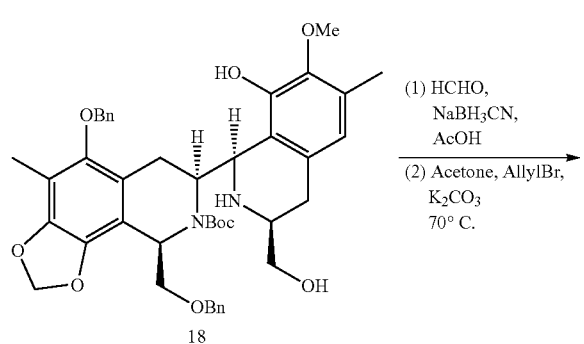

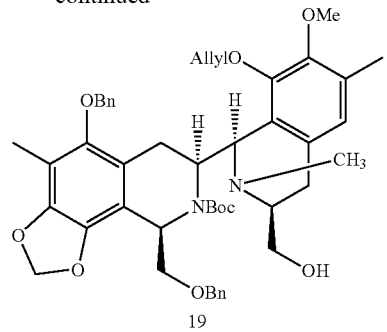

Under argon protection, the compound 18 (3.58 g, 4.85 mmol) was dissolved in a mixed solvent of CH$_3$CN/THF (40 mL:10 mL), 37% formaldehyde solution (3.93 g, 48.5 mmol) was added, and the reaction was stirred at room temperature for 20 minutes. NaBH$_3$CN (0.76 g, 12.13 mmol) was added, and the reaction was stirred at room temperature for 20 minutes. AcOH (0.69 mL, 12.13 mmol) was added, and the reaction was stirred at room temperature for 90 minutes. After the reaction was completed, the solvent was distilled off under reduced pressure, and saturated sodium bicarbonate was added. The solution was extracted three times with dichloromethane, and the combined organic phases was dried over anhydrous sodium sulfate, filtered, and the solvent was distilled off under reduced pressure to obtain a crude product. The crude product was dissolved in 50 mL of acetone, and K$_2$CO$_3$ (4.68 g, 33.95 mmol) and allyl bromide (4.11 g, 33.95 mmol) were added, and reacted at 65° C. under reflux for 4 hours. After the reaction was completed, the acetone solvent was distilled off under reduced pressure. Water was added and resulting system was extracted for three times with dichloromethane. The combined organic phases was dried over anhydrous sodium sulfate. The solution was filtered and the solvent was distilled off under reduced pressure, and flash column chromatography (EA:PE=1:3) purification was performed to afford 3.42 g of compound 19 with a two-step yield of 89%.

Compound 19: $^1$H NMR (400 MHz, CDCl$_3$) δ 7.42-7.21 (m, 8H), 7.08 (s, 2H), 6.72 (s, 1H), 6.37 (s, 1H), 5.90-5.84 (m, 2H), 5.60 (s, 1H), 5.44-5.01 (m, 3H), 4.65-4.48 (m, 4H), 4.43 (s, 1H), 4.31 (s, 1H), 4.12 (dd, J=14.2, 7.1 Hz, 1H), 3.94-3.69 (m, 3H), 3.60 (s, 3H), 3.48 (d, J=11.0 Hz, 1H), 3.13-2.64 (m, 4H), 2.59-2.32 (m, 5H), 2.23 (s, 3H), 2.14 (s, 3H), 1.48 (s, 9H).
$^{13}$C NMR (100 MHz, CDCl$_3$) δ 171.20, 155.76, 149.88, 148.59, 148.27, 144.26, 139.41, 138.39, 136.76, 134.88, 133.13, 130.37, 128.53, 128.37, 128.18, 128.15, 127.67, 127.39, 124.66, 120.93, 118.42, 112.25, 101.13, 79.97, 75.82, 74.49, 72.50, 64.06, 62.45, 59.97, 51.12, 45.34, 33.31, 21.09, 15.90, 14.23, 9.36.
HRMS (ESI): calcd. for C$_{47}$H$_{57}$N$_2$O$_9$ [M+H]$^+$ 793.4064; found 793.4068.

Example 11 Synthesis of Compound 20

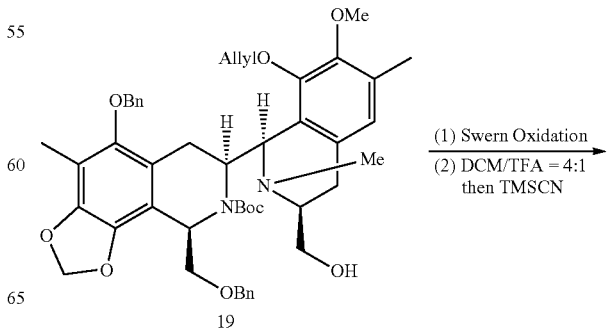

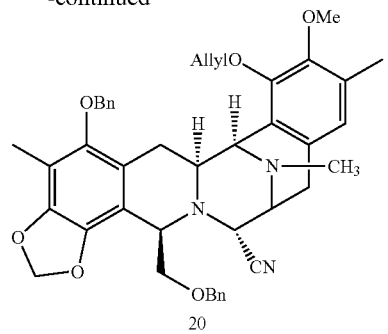

(COCl)₂ (1.21 mL, 14.75 mmol) was dissolved in 3 mL of anhydrous dichloromethane, and DMSO (2.10 mL, 29.52 mmol) dissolved in 3 mL of dichloromethane was slowly added dropwise under the protection of argon at −78° C. The reaction was kept at this temperature for 30 min, then compound 19 (2.92 g, 3.69 mmol) was dissolved in 30 mL of dichloromethane, and slowly added dropwise to the system. The reaction was kept at −78° C. for another 1 hour, and afterwards, DIPEA (4.50 mL, 25.83 mmol) was added, and was reacted at −78° C. for 30 min. After the reaction was completed, 15 mL of saturated ammonium chloride solution was added and extracted for three times with dichloromethane. The combined the organic phases was dried over anhydrous sodium sulfate, filtered, and the solvent was distilled off under reduced pressure. The crude product obtained was dissolved in 40 mL DCM/TFA=4:1 solvent mixture, and stirred to react at room temperature for 2 hours. TMSCN (1.83 g, 18.45 mmol) was added, and the reaction was stirred at room temperature for 2 hours. Then saturated sodium bicarbonate solution was slowly added, and extracted with dichloromethane for three times. The combined organic phases was dried over anhydrous sodium sulfate and filtered. The solvent was distilled off under reduced pressure, and flash column chromatography (EA/PE=1:3) purification was performed to afford 2.22 g of compound 20 with a two-step yield of 86%.

Compound 20: ¹H NMR (400 MHz, CDCl₃) δ 7.54-7.21 (m, 10H), 6.65 (s, 1H), 6.01 (ddt, J=16.4, 10.4, 6.0 Hz, 1H), 5.89 (dd, J=19.3, 1.3 Hz, 2H), 5.31 (dd, J=17.1, 1.4 Hz, 1H), 5.12 (d, J=10.3 Hz, 1H), 4.68 (dd, J=11.5, 6.4 Hz, 2H), 4.55-4.43 (m, 3H), 4.38-4.26 (m, 2H), 4.18 (dd, J=8.5, 2.1 Hz, 1H), 4.10 (d, J=2.2 Hz, 1H), 3.69 (s, 3H), 3.55 (dd, J=9.2, 2.5 Hz, 1H), 3.32 (dd, J=15.4, 2.2 Hz, 1H), 3.28-3.12 (m, 3H), 2.94 (dd, J=17.7, 8.1 Hz, 1H), 2.61 (d, J=17.7 Hz, 1H), 2.28 (s, 3H), 2.24 (s, 3H), 2.12 (s, 3H), 1.92 (dd, J=15.3, 11.6 Hz, 1H).

¹³C NMR (101 MHz, CDCl₃) δ 149.67, 148.70, 148.20, 144.36, 139.37, 138.39, 137.13, 134.28, 130.77, 130.23, 128.58, 128.39, 128.36, 128.25, 127.52, 127.37, 124.66, 124.06, 121.47, 118.79, 117.95, 112.80, 112.21, 101.13, 76.43, 75.21, 73.83, 73.39, 61.96, 59.99, 57.33, 57.25, 57.01, 55.53, 41.78, 26.40, 25.51, 15.89, 9.33.

HRMS (ESI): calcd. for C₄₃H₄₆N₃O₆ [M+H]⁺ 700.3387; found 700.3390.

Example 12 Synthesis of Compound 21

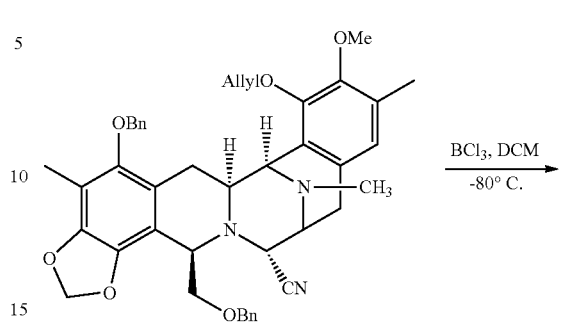

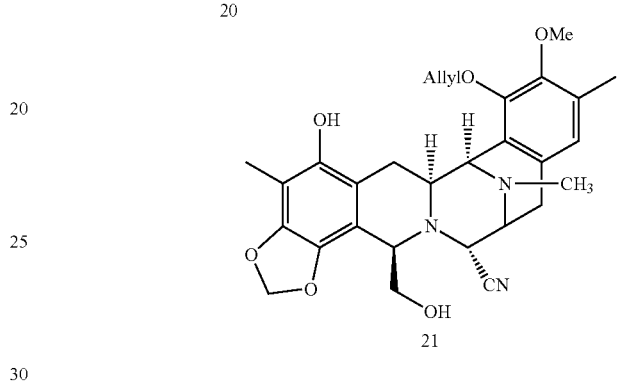

Under argon protection, the compound 20 (0.5 g, 0.715 mmol) was dissolved in 10 mL of anhydrous dichloromethane, and cooled to −80° C. 1M BCl₃ solution in dichloromethane (5.01 mL, 5.01 mmol) was added dropwise, and the temperature was maintained for 1 hour. After the reaction is completed, 5 mL of methanol was added to quench the reaction at −80° C., the solvent was distilled off under reduced pressure, and saturated sodium bicarbonate solution was added, and extracted three times with dichloromethane. The combined organic phases was dried over anhydrous sodium sulfate. Altered, and the solvent was distilled off under reduced pressure. Flash column chromatography (DCM/MeOH=20:1) was performed to give 0.30 g of compound 21 in 81% yield.

Compound 21: ¹H NMR (400 MHz, CDCl₃) δ 6.68 (s, 1H), 6.10 (ddd, J=16.1, 10.8, 5.7 Hz, 1H), 5.85 (d, J=21.2 Hz, 2H), 5.43 (dd, J=17.2, 1.5 Hz, 1H), 5.26 (dd, J=10.4, 1.0 Hz, 1H), 4.96 (s, 1H), 4.71 (dd, J=12.6, 5.5 Hz, 1H), 4.41 (ddt, J=12.7, 5.8, 1.2 Hz, 1H), 4.14 (d, J=2.0 Hz, 1H), 4.05 (d, J=2.5 Hz, 1H), 3.97 (t, J=3.0 Hz, 1H), 3.77 (s, 3H), 3.63 (dd, J=11.1, 3.5 Hz, 1H), 3.43 (d, J=10.2 Hz, 1H), 3.39-3.30 (m, 2H), 3.13-2.98 (m, 2H), 2.51 (d, J=18.1 Hz, 1H), 2.33 (s, 3H), 2.21 (s, 3H), 2.07 (s, 3H), 1.81 (dd, J=15.4, 11.9 Hz, 1H).

Compound 21: ¹³C NMR (100 MHz, CDCl₃) δ 149.58, 149.10, 145.14, 144.40, 136.49, 134.18, 131.21, 129.56, 124.95, 123.59, 117.80, 117.68, 113.36, 113.09, 106.29, 100.87, 73.58, 63.71, 60.21, 60.17, 58.08, 57.20, 56.62, 55.37, 41.78, 25.80, 25.65, 15.80, 8.82.

HRMS (ESI): calcd. for C₂₉H₃₄N₃O₆ [M+H]⁺ 520.2448; found 520.2450.

Example 13 Synthesis of Compound 22

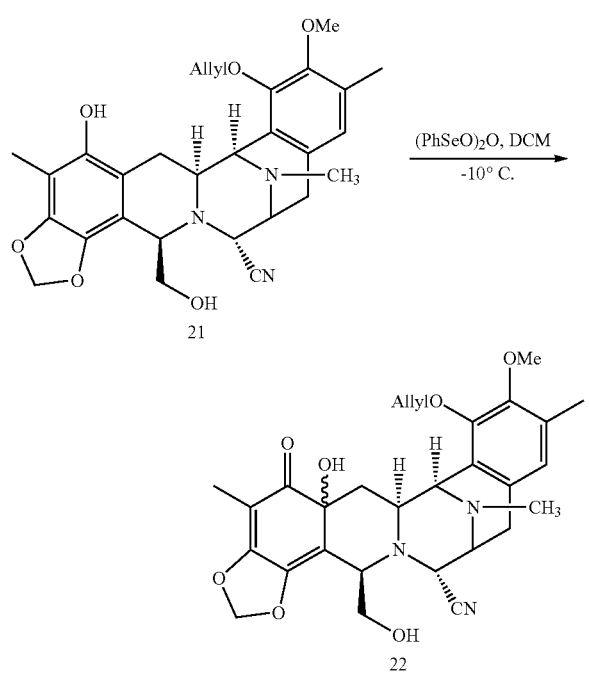

Under argon protection, the compound 21 (0.6 g, 1.16 mmol) was dissolved in 30 mL of anhydrous dichloromethane, and cooled to −10° C. (PhSeO)$_2$O (0.37 g, 1.16 mmol) was dissolved in 10 mL of dichloromethane, slowly added to the reaction system and reacted at −10° C. for 10 minutes. After the reaction was completed, saturated sodium bicarbonate solution was added and extracted three times with dichloromethane. The combined organic phases was dried with anhydrous sodium sulfate. Altered, and the solvent was distilled off under reduced pressure. Flash column chromatography (EA/PE=1:1) purification was performed to afford 0.53 g of compound 22, yield 86%.

Compound 22 isomer 1: $^1$H NMR (400 MHz, CDCl$_3$) δ 6.62 (s, 1H), 5.99 (ddt, J=16.3, 10.4, 5.8 Hz, 1H), 5.86 (s, 1H), 5.76 (s, 1H), 5.29 (dd, J=17.1, 1.5 Hz, 1H), 5.20 (dd, J=10.4, 1.3 Hz, 1H), 4.56 (ddt, J=12.5, 5.6, 1.3 Hz, 1H), 4.29 (ddt, J=12.5, 6.1, 1.2 Hz, 1H), 4.24 (d, J=2.8 Hz, 1H), 4.09 (dd, J=13.4, 1.2 Hz, 1H), 4.03-3.94 (m, 2H), 3.75 (dt, J=11.9, 2.8 Hz, 1H), 3.68 (s, 3H), 3.62 (d, J=2.7 Hz, 1H), 3.39 (d, J=8.7 Hz, 1H), 3.03-2.84 (m, 2H), 2.54 (d, J=17.9 Hz, 1H), 2.22 (s, 3H), 2.20 (s, 3H), 2.12 (dd, J=14.0, 2.8 Hz, 1H), 1.80 (s, 3H).

$^{13}$C NMR (101 MHz, CDCl$_3$) δ 200.47, 159.83, 149.49, 148.70, 137.64, 134.05, 130.63, 130.12, 124.74, 123.84, 117.81, 116.66, 113.61, 105.04, 100.80, 73.26, 72.25, 59.94, 58.33, 57.27, 56.71, 56.65, 56.04, 55.21, 41.55, 41.48, 25.49, 15.92, 7.16.

HRMS (ESI): calcd. for C$_{29}$H$_{34}$H$_3$O$_7$ [M+H]$^+$ 536.2397; found 536.2400.

Compound 22 isomer 2: $^1$H NMR (400 MHz, CDCl$_3$) δ 6.69 (s, 1H), 6.01 (ddt, J=16.5, 10.4, 5.8 Hz, 1H), 5.85 (d, J=0.7 Hz, 2H), 5.32 (dd, J=17.1, 1.5 Hz, 1H), 5.18 (dd, J=10.3, 1.3 Hz, 1H), 4.72 (dd, J=12.6, 5.5 Hz, 1H), 4.33 (dd, J=12.6, 6.1 Hz, 1H), 4.09 (d, J=2.6 Hz, 1H), 4.01 (d, J=2.3 Hz, 1H), 3.96 (s, 3H), 3.87 (t, J=3.4 Hz, 1H), 3.78 (dd, J=11.6, 4.0 Hz, 1H), 3.61 (dd, J=11.7, 2.9 Hz, 1H), 3.30 (dd, J=12.9, 5.1 Hz, 2H), 3.01 (dd, J=18.0, 7.9 Hz, 1H), 2.60 (d, J=17.9 Hz, 1H), 2.29 (s, 3H), 2.23 (s, 3H), 2.19 (dd, J=10.7, 4.8 Hz, 1H), 1.98 (dd, J=15.4, 8.1 Hz, 1H), 1.80 (s, 3H).

$^{13}$C NMR (100 MHz, CDCl$_3$) δ 198.75, 158.94, 149.31, 149.24, 140.37, 134.11, 131.27, 130.14, 125.10, 122.64, 117.80, 116.96, 111.09, 104.36, 101.64, 73.73, 70.32, 61.58, 60.64, 58.42, 57.96, 57.31, 55.24, 55.20, 41.85, 36.37, 25.66, 15.83, 7.32.

HRMS (ESI): calcd. for C$_{29}$H$_{34}$N$_3$O$_7$ [M+H]$^+$ 536.2397; found 536.2400.

Example 14 Synthesis of Compound 24

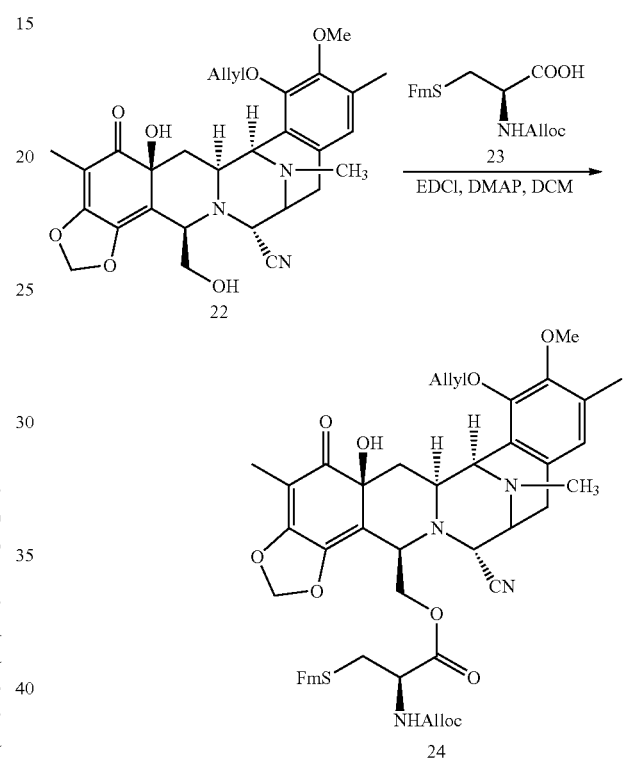

Under argon protection, compound 22 (180 mg, 0.336 mmol), compound 23 (387 mg, 1.01 mmol), EDCI (321 mg, 1.68 mmol) and DMAP (205 mg, 1.68 mmol) were mixed and dissolved in 30 mL of anhydrous dichloromethane, and stirred at room temperature for 5 hours. After the reaction was completed, saturated ammonium chloride solution was added and extracted for three times with dichloromethane. The combined organic phases was dried over anhydrous sodium sulfate, filtered, and the solvent was distilled off under reduced pressure. Flash column chromatography (EA/PE=1:2) purification was performed to afford 261 mg of compound 24, yield 85%.

Compound 24: $^1$H NMR (400 MHz, CDCl$_3$) δ 7.74 (d, J=7.5 Hz, 2H), 7.66 (d, J=7.4 Hz, 2H), 7.41-7.35 (m, 2H), 7.34-7.27 (m, 2H), 6.54 (d, J=11.7 Hz, 1H), 6.03-5.84 (m, 2H), 5.71-5.58 (m, 3H), 5.37-5.13 (m, 5H), 4.68 (d, J=12.5 Hz, 1H), 4.60-4.47 (m, 4H), 4.39 (dd, J=12.7, 5.0 Hz, 1H), 4.28 (dd, J=12.5, 6.1 Hz, 1H), 4.11 (t, J=6.0 Hz, 1H), 3.95 (dd, J=9.1, 6.3 Hz, 1H), 3.87 (d, J=2.5 Hz, 1H), 3.71 (s, 1H), 3.67 (s, 1H), 3.27 (t, J=8.5 Hz, 1H), 3.15 (d, J=6.3 Hz, 1H), 2.97 (d, J=3.0 Hz, 1H), 2.84 (dd, J=17.9, 8.4 Hz, 1H), 2.39 (d. J=17.8 Hz, 1H), 2.19 (s, 1H), 2.16 (d, J=4.1 Hz, 1H), 1.77 (d, J=6.9 Hz, 1H).

$^{13}$C NMR (101 MHz, CDCl$_3$) δ 200.23, 170.52, 160.06, 155.82, 149.48, 148.68, 145.62, 145.59, 145.54, 141.11, 141.07, 138.54, 138.49, 134.04, 132.44, 130.67, 129.97, 127.69, 127.14, 124.84, 124.80, 124.62, 123.72, 119.93, 118.01, 117.79, 116.82, 111.54, 104.87, 101.04, 73.22, 72.25, 66.02, 63.77, 59.92, 58.11, 56.61, 56.56, 56.09, 55.20, 54.02, 46.95, 46.88, 41.81, 41.44, 35.95, 35.23, 31.91, 29.29, 25.52, 22.68, 7.12.

HRMS (ESI): calcd. for C$_{50}$H$_{53}$N$_4$O$_{10}$S [M+H]$^+$ 901.3482; found 901.3484.

Example 15 Synthesis of Compound 25

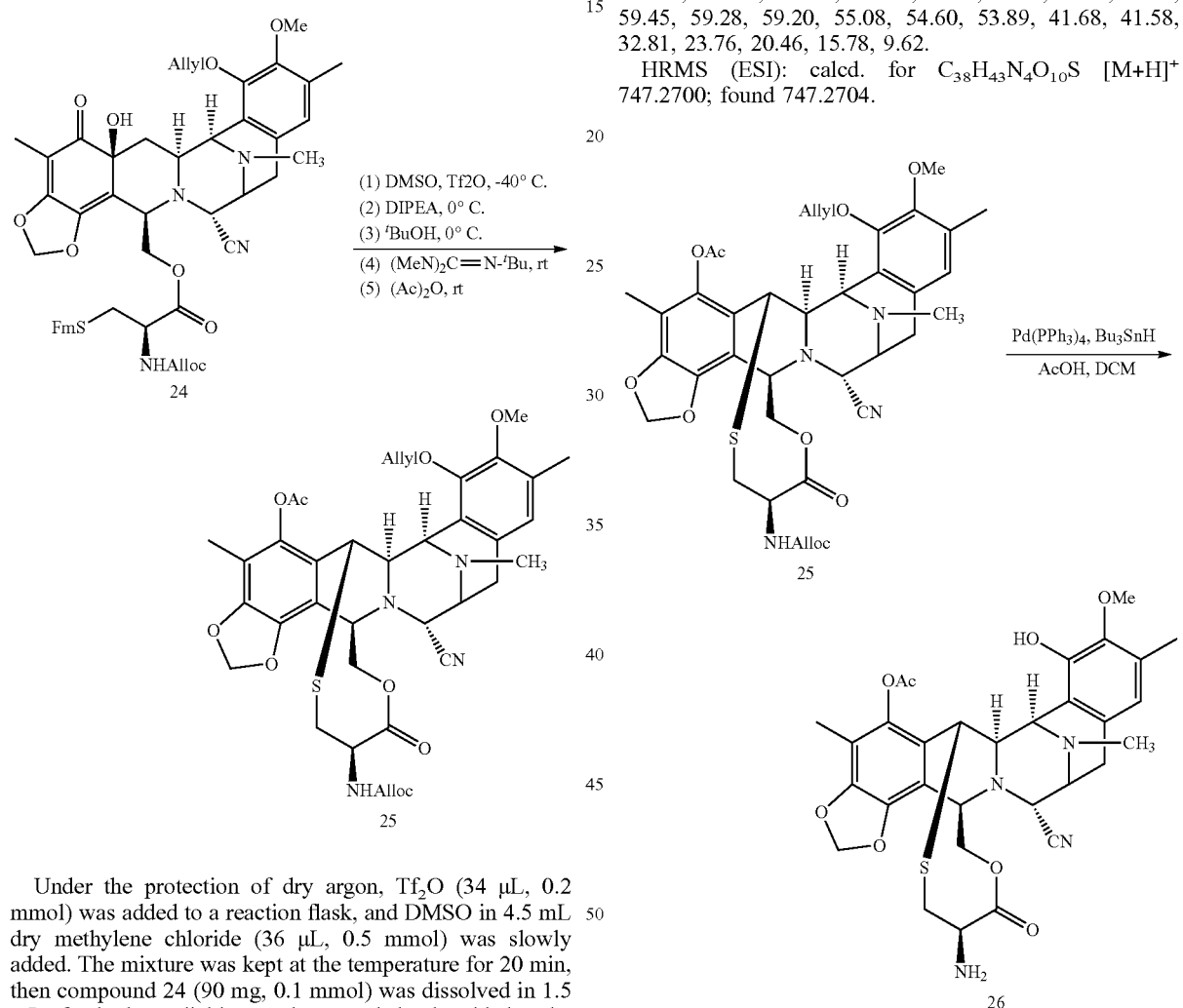

Under the protection of dry argon, Tf$_2$O (34 μL, 0.2 mmol) was added to a reaction flask, and DMSO in 4.5 mL dry methylene chloride (36 μL, 0.5 mmol) was slowly added. The mixture was kept at the temperature for 20 min, then compound 24 (90 mg, 0.1 mmol) was dissolved in 1.5 mL of anhydrous dichloromethane, and slowly added to the system while the system was maintained at −78° C. After the addition was completed, the system was warmed to −40° C. for 40 min, then DIPEA (139 μL, 0.8 mmol) was slowly added dropwise. The system was warmed to 0° C. for 45 min, then $^t$BuOH (29 μL, 0.3 mmol) was added at 0° C. for 40 min. The mixture was moved to room temperature after the reaction was completed, and (MeN)$_2$C=N-$^t$Bu (141 μL, 0.7 mmol) was added at room temperature for 40 min. (Ac)$_2$O (38 μL, 0.4 mmol) was added and stirred at room temperature for 15 min. After the reaction was completed, saturated ammonium chloride solution was added and extracted for three times with dichloromethane. The combined organic phases was dried over anhydrous sodium sulfate. The solvent was distilled off under reduced pressure, and flash column chromatography (EA/PE=1:3) purification was performed to afford 36 mg of compound 25, yield 49%.

Compound 25: $^1$H NMR (400 MHz, CDCl$_3$) δ 6.78 (s, 1H), 6.15-5.88 (m, 4H), 5.45 (d, J=17.1 Hz, 1H), 5.32 (d, J=17.2 Hz, 1H), 5.25 (d, J=10.4 Hz, 2H), 5.02 (d, J=11.6 Hz, 1H), 4.81 (d, J=9.7 Hz, 2H), 4.65-4.44 (m, 3H), 4.39-4.27 (m, 2H), 4.26-4.12 (m, 4H), 3.80 (s, 3H), 3.46-3.35 (m, 2H), 2.98-2.88 (m. J=12.3 Hz, 2H), 2.27 (s, 6H), 2.20 (s, 3H), 2.13 (d, J=15.7 Hz, 1H), 2.03 (s, 3H).

$^{13}$C NMR (100 MHz, CDCl$_3$) δ 170.41, 168.60, 155.43, 150.85, 148.87, 145.77, 140.92, 140.38, 134.53, 132.88, 131.72, 129.97, 124.71, 124.62, 120.22, 118.02, 118.00, 116.64, 113.54, 113.38, 102.02, 72.92, 65.86, 61.34, 60.50, 59.45, 59.28, 59.20, 55.08, 54.60, 53.89, 41.68, 41.58, 32.81, 23.76, 20.46, 15.78, 9.62.

HRMS (ESI): calcd. for C$_{38}$H$_{43}$N$_4$O$_{10}$S [M+H]$^+$ 747.2700; found 747.2704.

Under argon protection, the compound 25 (108 mg, 0.145 mmol) and Pd (PhPPh$_3$)$_4$ (66.84 mg, 0.058 mmol) were dissolved in 5 mL of dichloromethane. Bu$_3$SnH (0.12 ml, 0.434 mmol) and AcOH (0.05 ml, 0.868 mmol) were added and stirred at room temperature for 3 hours. After the reaction was completed, saturated sodium bicarbonate solution was added, and extracted three times with dichloromethane. The combined organic phases was dried over anhydrous sodium sulfate, filtered, and the solvent was distilled off under reduced pressure. Flash column chromatography (DCM/MeOH=10:1) purification was performed to afford 76 mg of compound 26, yield 85%.

Compound 26: $^1$H NMR (400 MHz, CDCl$_3$) δ 6.51 (s, 1H), 6.07 (d, J=1.3 Hz, 1H), 5.98 (d, J=1.3 Hz, 1H), 5.01 (d, J=11.5 Hz, 1H), 4.52 (s, 1H), 4.25 (d, J=4.7 Hz, 2H), 4.18 (d, J=2.5 Hz, 1H), 4.13 (dd, J=11.6, 1.8 Hz, 1H), 3.78 (s, 2H), 3.43-3.38 (m, 2H), 3.32 (s, 1H), 2.92-2.87 (m, 2H), 2.30 (s, 3H), 2.28 (s, 3H), 2.22 (m, 2H), 2.18 (s, 3H), 2.03 (s, 3H).

$^{13}$C NMR (100 MHz, CDCl$_3$) δ 174.11, 168.65, 147.91, 145.69, 142.97, 141.02, 140.34, 130.51, 129.41, 120.80, 120.44, 118.25, 118.17, 113.71, 113.38, 101.95, 61.39, 60.24, 60.12, 59.35, 59.15, 54.68, 54.62, 53.98, 41.78, 41.52, 34.22, 23.83, 20.60, 15.70, 9.64.

HRMS (ESI): calcd. for C$_{31}$H$_{35}$N$_4$O$_8$S [M+H]$^+$ 623.2176; found 623.2180.

Example 17 Synthesis of Compound 28

Compound 28: $^1$H NMR (400 MHz, CDCl$_3$) δ 6.49 (s, 1H), 6.11 (d, J=1.3 Hz, 1H), 6.02 (d, J=1.3 Hz, 1H), 5.78 (s, 1H), 5.09 (d, J=11.4 Hz, 1H), 4.66 (s, 1H), 4.39 (s, 1H), 4.28 (d, J=5.0 Hz, 1H), 4.21 (dd, J=11.4, 1.8 Hz, 1H), 4.16 (d, J=1.9 Hz, 1H), 3.75 (s, 3H), 3.55 (d, J=5.0 Hz, 1H), 3.43 (d, J=8.3 Hz, 1H), 2.92 (d, J=9.6 Hz, 1H), 2.82 (s, 1H), 2.70 (d, J=17.8 Hz, 1H), 2.56 (d, J=13.9 Hz, 1H), 2.32 (s, 3H), 2.24 (s, 3H), 2.15 (s, 3H), 2.04 (s, 3H).

$^{13}$C NMR (100 MHz, CDCl$_3$) δ 186.71, 168.56, 160.52, 147.21, 146.40, 143.01, 141.67, 140.70, 130.41, 129.90, 121.69, 120.04, 117.89, 117.12, 113.50, 113.39, 102.25, 61.76, 61.40, 60.33, 59.80, 58.93, 54.61, 43.24, 41.63, 36.88, 24.16, 20.36, 15.81, 9.68.

HRMS (ESI): calcd. for C$_{31}$H$_{32}$N$_3$O$_9$S [M+H]$^+$ 622.1859; found 622.1862.

Example 18 Synthesis of Compound 30

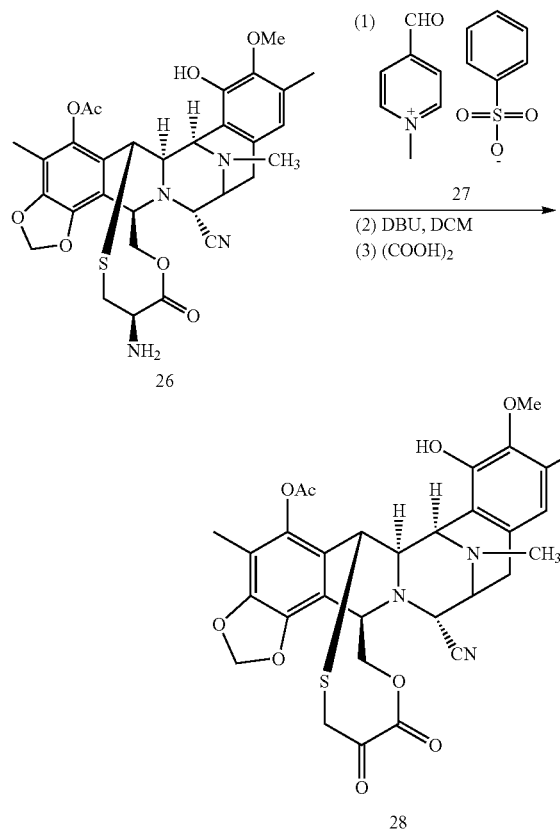

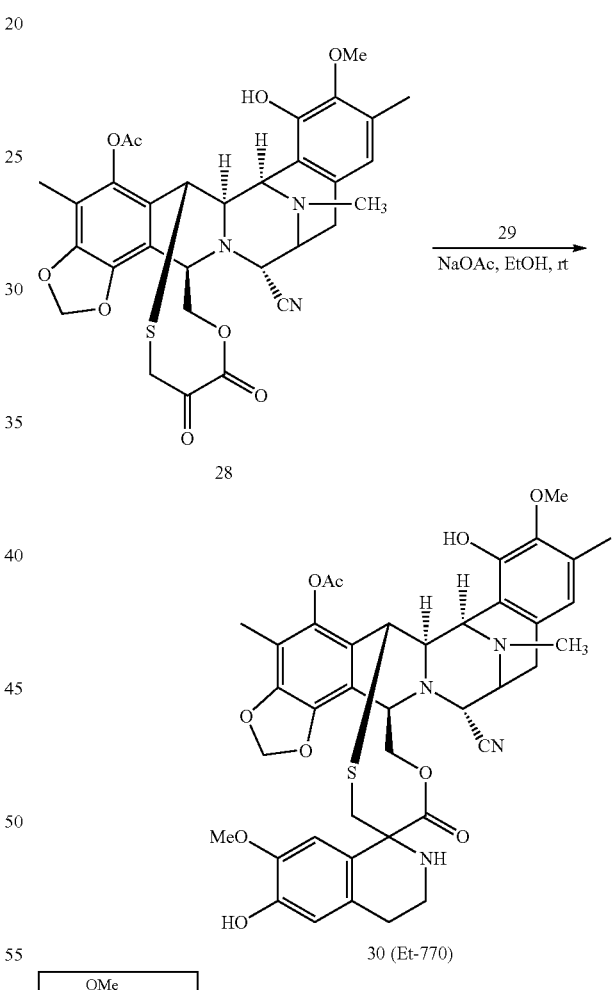

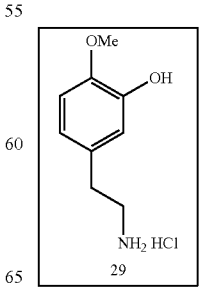

Under the protection of argon, the compound 27 (44 mg, 0.157 mmol) was dissolved in 1.5 mL of anhydrous DMF. The compound 26 (14 mg, 0.0225 mmol) dissolved in 1.5 mL of DCM was added to the system and stirred at room temperature for 4 hours. DBU (8.6 mg, 0.0562 mmol) was dissolved in 0.5 mL of anhydrous DCM, and slowly added to the system at 0° C. At this time, the reaction solution was black. After 20 minutes, 1 mL of saturated oxalic acid solution was added at 0° C., and the reaction was allowed to stand at room temperature for 45 min. After the reaction was completed, sodium bicarbonate solution was added under 0° C., and extracted three times with ether. The combined organic phases was dried with anhydrous sodium sulfate, filtered, and the solvent was distilled off under reduced pressure. Flash column chromatography (EA/PE=1:2) purification was performed to afford 8.0 mg of compound 28, yield 57%.

Under the protection of argon, compound 28 (29 mg, 0.0467 mmol), compound 29 (95 mg, 0.467 mmol) and NaOAc (43 mg, 0.514 mmol) were mixed and dissolved in 5 mL of anhydrous ethanol, and the reaction was stirred at room temperature for 5 hours. After the reaction was completed, the solvent was distilled off under reduced pressure, and water was added. The mixture was extracted three times with ethyl acetate, and the combined organic phases was dried over anhydrous sodium sulfate, filtered, and the solvent was distilled off under reduced pressure. Flash column chromatography (DCM/MeOH=20:1) purification was performed to afford 33 mg of compound 30, yield 92%.

Compound 30: $^1$H NMR (400 MHz, CDCl$_3$) δ 6.60 (s, 1H), 6.48 (s, 1H), 6.42 (s, 1H), 6.05 (s, 1H), 5.98 (s, 1H), 5.84 (s, 1H), 5.02 (d, J=11.5 Hz, 1H), 4.58 (s, 1H), 4.34 (s, 1H), 4.28 (d, J=4.8 Hz, 1H), 4.18 (d, J=2.4 Hz, 1H), 4.13 (d, 7=9.7 Hz, 1H), 3.78 (d, J=14.4 Hz, 3H), 3.62 (s, 3H). 3.51 (d, J=4.5 Hz, 1H), 3.44-3.40 (m, 1H), 3.20-3.10 (m, 1H), 2.94 (d, J=5.1 Hz, 2H), 2.88 (s, 1H), 2.68 (s, 1H), 2.50 (d, J=15.4 Hz, 1H), 2.36 (d, J=17.7 Hz, 1H), 2.33 (s, 3H), 2.27 (s, 3H), 2.20 (s, 3H), 2.04 (s, 3H).

$^{13}$C NMR (100 MHz, CDCl$_3$) δ 172.55, 168.21, 147.86, 145.33, 144.60, 144.36, 143.07, 141.34, 140.13, 130.78, 129.42, 129.07, 125.62, 121.15, 120.73, 118.17, 118.14, 114.14, 114.07, 113.43, 109.80, 101.87, 64.62, 61.12, 60.37, 60.06, 59.67, 59.57, 55.19, 54.71, 54.62, 42.16, 41.87, 41.62, 39.67, 28.72, 24.18, 20.45, 15.84, 9.74.

HRMS (ESI): calcd. for C$_{40}$H$_{43}$N$_4$O$_{10}$S [M+H]$^+$ 771.2700; found 771.2703.

Example 19: Synthesis of Et-743

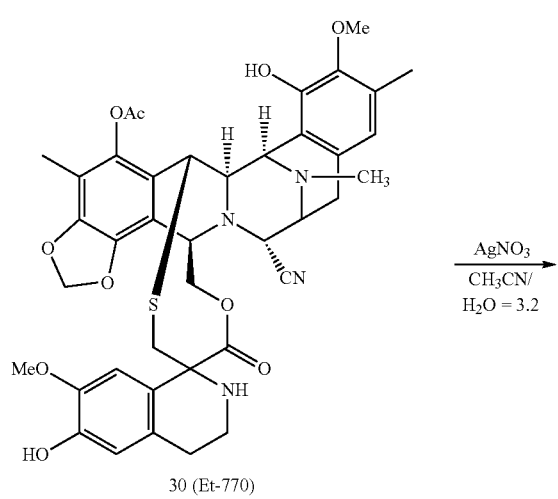

30 (Et-770)

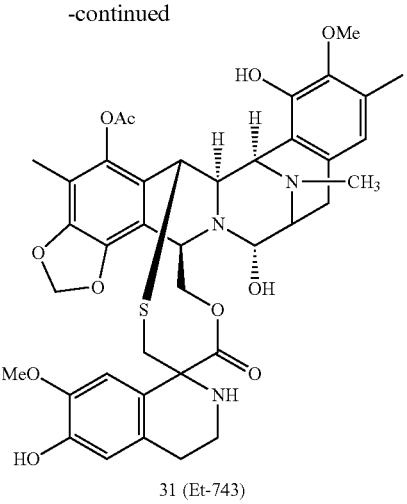

31 (Et-743)

Under the protection of argon, the compound 29 (7.7 mg, 0.01 mmol) was dissolved in 1 mL of a mixed solvent of acetonitrile and water prepared in proportion. AgNO$_3$ (32.3 mg, 0.19 mmol) was added, and the reaction was stirred at room temperature for 24 h, 1 mL saturated sodium chloride and saturated sodium bicarbonate solution were added respectively, and stirred for 10 min. The mixture was extracted three times with ethyl acetate, and the combined organic phases was dried over anhydrous sodium sulfate, filtered, and the solvent was distilled off under reduced pressure. Flash column chromatography (DCM/MeOH=20: 1) purification was performed to afford 7.2 mg of compound 31 (Et-743). Yield 95%.

$^1$H NMR (400 MHz, CDCl$_3$) δ 6.63 (s, 1H), 6.48 (s, 1H), 6.43 (s, 1H), 6.03 (d, J=1.1 Hz, 1H), 5.95 (d, J=1.1 Hz, 1H), 5.85 (s, 1H), 5.12 (d, J=11.4 Hz, 2H), 4.89 (s, 1H), 4.54 (d, J=25.4 Hz, 2H), 4.06 (dd, J=11.4, 2.1 Hz, 2H), 3.82 (s, 3H), 3.62 (s, 3H), 3.46-3.31 (m, 2H), 3.25-3.09 (m, 2H), 3.03-2.78 (m, 4H), 2.35 (s, 3H), 2.27 (s, 3H), 2.16 (s, 3H), 2.03 (s, 3H).

HRMS (ESI): calcd. for C$_{39}$H$_{42}$N$_3$O$_{10}$S [M−OH]$^+$ 744.2591; found 744.2594.

Compound 15 can also be synthesized from compound 9 according to the following optimized route. Specific operation examples and compound data are as follows:

Example 20 Synthesis of Compound 32

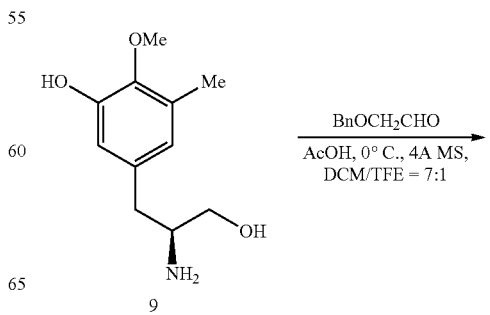

9

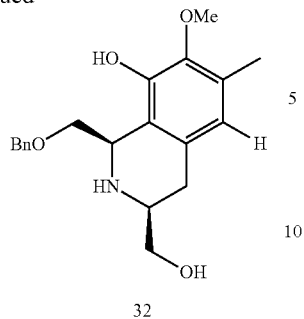

32

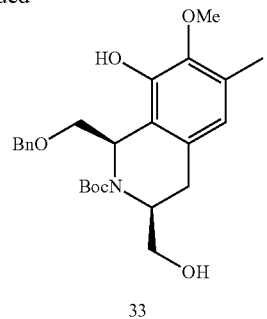

33

Under the protection of argon, the compound 9 (10.1 g, 47.86 mmol) was dissolved in a mixed solvent of DCM (175 ml) and TFE (25 ml). Benzyloxyacetaldehyde (9.3 g, 62.22 mmol) and 4A MS (10.1 g) were added, and AcOH (0.72 g, 12.0 mmol) was slowly added dropwise at −10° C. The reaction was maintained at −10° C. for 4 hours, and then warmed to 0° C. for another 4 hours. After the reaction was completed, the molecular sieve was removed by filtration through celite. Saturated sodium bicarbonate solution was added, extracted three times with dichloromethane, and the organic phases was combined. After the solvent was distilled off under reduced pressure, the residue was purified through flash column chromatography (DCM/MeOH=20:1) to afford 14.6 g of white solid compound 32, yield 89%.

Compound 32: $^1$H NMR (400 MHz, CDCl$_3$) δ 7.36-7.26 (m, 5H), 6.46 (s, 1H), 4.54 (q, J=12.1 Hz, 2H), 4.44 (t, J=4.8 Hz, 1H), 3.99 (dd, J=9.2, 4.3 Hz, 1H), 3.80 (dd, J=9.2, 5.9 Hz, 1H), 3.76 (s, 3H), 3.72 (dd, J=10.8, 3.8 Hz, 1H), 3.50 (dd, J=10.8, 7.0 Hz, 1H), 2.98-2.90 (m, 1H), 2.55-2.47 (m, 2H), 2.24 (s, 3H).

$^{13}$C NMR (100 MHz, CDCl$_3$) δ 146.21, 143.90, 138.10, 132.60, 128.68, 128.36, 127.76, 127.65, 122.26, 120.70, 73.73, 73.23, 66.18, 60.57, 54.04, 53.28, 32.56, 15.64.

HRMS (ESI): calcd. for $C_{20}H_{26}NO_4[M+H]^+$ 344.1862; found 344.1864.

Example 21 Synthesis of Compound 33

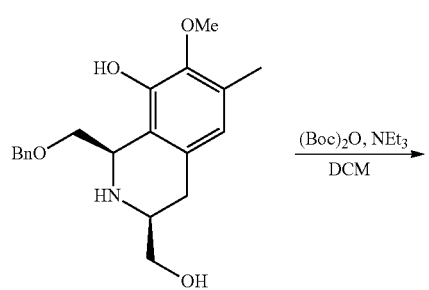

Under argon protection, the compound 32 (1.2 g, 3.5 mmol) was dissolved in 35 ml of anhydrous DCM, (Boc)$_2$O (0.92 g, 4.2 mmol) and NEt$_3$ (0.97 ml, 7.0 mmol) were added, and stirred at room temperature for 5 hours. After the reaction was completed, 50 ml of water was added, extracted three times with dichloromethane. The combined organic phases was dried over anhydrous sodium sulfate, the solvent was distilled off under reduced pressure, and flash column chromatography (EA/PE=1:4) purification was performed to provide 1.5 g of white foam product 33, yield 97%.

Compound 33: $^1$H NMR (400 MHz, CDCl$_3$) δ 7.33-7.25 (m, 5H), 6.53 (s, 1H), 6.24 (d, J=27.2 Hz, 1H), 5.90 (d, J=110.2 Hz, 1H), 4.89-4.62 (m, 1H), 4.55 (d, J=11.7 Hz, 1H), 4.23 (d, J=23.1 Hz, 1H), 3.96 (d, J=16.5 Hz, 1H), 3.76 (s, 1H), 3.67 (dd, J=21.7, 12.9 Hz, 2H), 3.61-3.30 (m, 2H), 3.11-2.69 (m, 2H), 2.26 (s, 3H), 1.45 (s, 9H).

$^{13}$C NMR (100 MHz, CDCl$_3$) δ 155.90 (s), 145.20, 143.87, 137.72, 130.57, 130.51, 129.72, 128.35, 127.69, 121.44, 119.82, 80.48, 72.66, 71.74, 71.01, 65.87, 64.64 60.66, 53.43, 49.57, 48.10, 28.42, 15.72.

HRMS (ESI): calcd. for $C_{25}H_{33}NO_6Na$ $[M+Na]^+$ 466.2206; found 466.2205.

Example 22 Synthesis of Compound 34

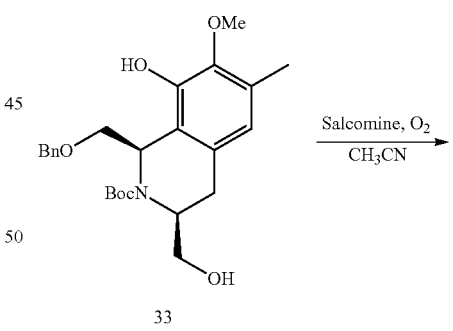

33

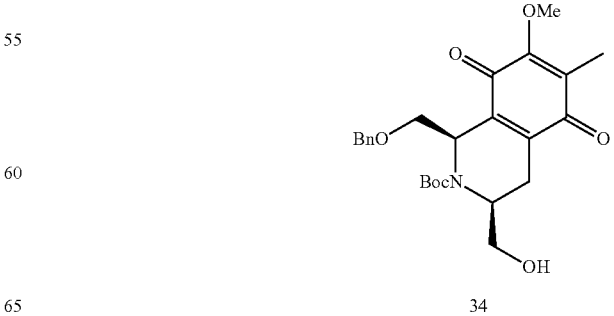

34

The compound 33 (5.0 g, 11.3 mmol) was dissolved in 100 ml of anhydrous acetonitrile, a salcomine catalyst (0.36 g, 1.1 mmol) was added, and the atmosphere was exchanged with oxygen for 3 times, so that the reaction was conducted for 1 hour under oxygen atmosphere. The black solid catalyst was filtered off after the reaction was completed, and acetonitrile was distilled off under reduced pressure. The target product which appeared yellow on a column was purified through flash column chromatography (EA/PE=1:4) to give 4.4 g of yellow product 34, yield 85%.

Compound 34: $^1$H NMR (400 MHz, CDCl$_3$) δ 7.24-7.11 (m, 5H), 5.20 (d, J=74.0 Hz, 1H), 4.44 (s, 2H), 4.34 (d, J=11.8 Hz, 1H), 3.80 (s, 3H), 3.77-3.64 (m, 2H), 3.59 (d, J=7.1 Hz, 1H), 3.45 (m, 1H), 3.34 (m, 1H), 2.59 (d, J=19.0 Hz, 1H), 2.46 (ddd, J=19.1, 7.5, 2.0 Hz, 1H), 1.82 (s, 3H), 1.35 (s, 9H).

$^{13}$C NMR (101 MHz, CDCl$_3$) δ 186.29, 181.04, 155.60, 155.05, 140.33, 137.07, 136.74, 136.30, 128.38, 127.87, 127.84, 80.80, 73.31, 72.39, 65.03, 60.69, 50.12, 49.22, 48.41, 28.29, 22.84, 8.63.

HRMS (ESI): calcd. for C$_{25}$H$_{31}$NO$_7$Na [M+Na]$^+$ 480.1998; found 480.2003.

Example 23 Synthesis of Compound 35

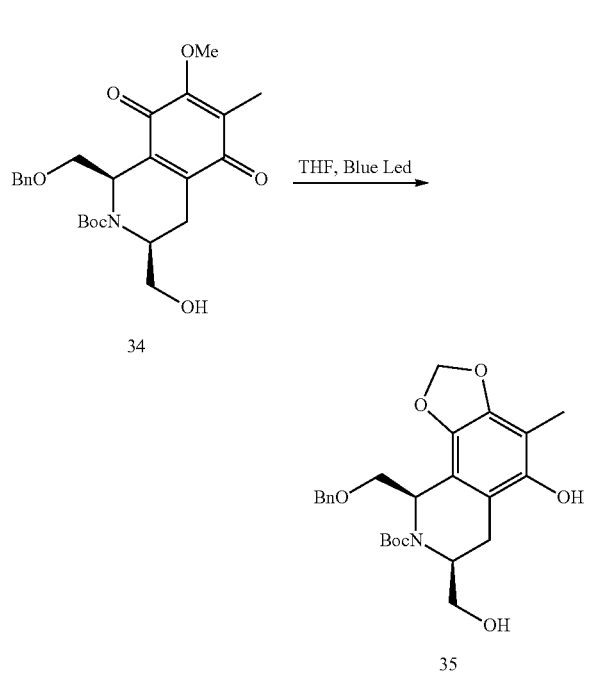

Under argon protection, the compound 34 (2.0 g, 4.38 mmol) was dissolved in 44 ml of anhydrous tetrahydrofuran, and the mixture was stirred at room temperature for 2 hours under blue light irradiation. After the reaction was completed, the solvent was distilled off under reduced pressure, and flash column chromatography (EA/PE=1:2) purification was performed to afford 1.5 g of compound 35 as a white foamy solid, yield 75%.

Compound 35: $^1$H NMR (400 MHz, CDCl$_3$) δ 7.36-7.22 (m, 5H), 5.80 (d, J=10.0 Hz, 2H), 5.63 (s, 1H), 5.45 (d, J=22.8 Hz, 1H), 4.75-4.37 (m, 3H), 3.95-3.69 (m, 4H), 3.54 (s, 1H), 2.78 (d, J=35.5 Hz, 2H), 2.08 (s, 3H), 1.45 (s, 9H).

$^{13}$C NMR (100 MHz, CDCl$_3$) δ 155.88, 146.22, 144.13, 137.54, 136.75, 128.33, 127.81, 127.76, 113.06, 112.48, 106.86, 100.72, 80.68, 72.98, 71.21, 70.72, 67.99, 65.66, 64.67, 28.40, 22.96, 8.90.

HRMS (ESI): calcd. for C$_{25}$H$_{33}$NO$_6$Na [M+Na]$^+$ 480.1998; found 480.1999.

Example 24 Synthesis of Compound 15

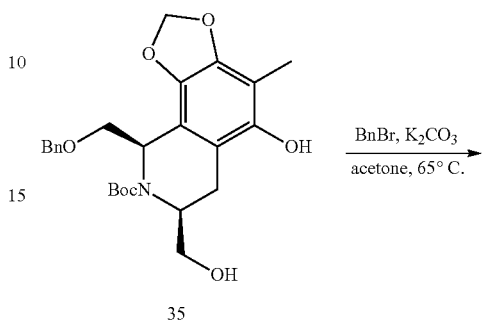

The compound 35 (1.5 g, 3.28 mmol) was dissolved in 30 ml of acetone, BnBr (1.12 g, 6.56 mmol) and K$_2$CO$_3$ (0.91 g, 6.56 mmol) were added, and the reaction was refluxed at 65° C. for 5 hours. After the reaction was completed, the solvent was distilled off under reduced pressure, and the residue was extracted three times with dichloromethane. The combined organic phases was dried over anhydrous sodium sulfate, the solvent was distilled off by rotary evaporation under reduced pressure, and flash column chromatography (EA/PE=1:4) purification was performed to afford 1.68 g viscous compound 15, yield 94%.

Compound 15: [α]$_D^{24.6}$=1.60 (c=1.0, CHCl$_3$) $^1$H NMR (400 MHz, CDCl$_3$) δ 7.45-7.25 (m, 10H), 5.86 (t, J=5.4 Hz, 2H), 5.77-5.42 (m, 1H), 4.73 (s, 2H), 4.71-4.57 (m, 1H), 4.52 (d, J=11.8 Hz, 1H), 4.28 (d, J=37.5 Hz, 1H), 3.93-3.68 (m, 3H), 3.57-3.19 (m, 2H), 2.99-2.69 (m, 2H), 2.18 (s, 3H), 1.46 (s, 9H).

$^{13}$C NMR (100 MHz, CDCl$_3$) δ 155.84, 149.26, 144.52, 139.33, 137.68, 137.12, 128.60, 128.34, 128.23, 128.02, 127.76, 127.74, 80.53, 75.22, 72.89, 70.58, 64.36, 52.52, 49.88, 48.51, 28.42, 23.44, 9.50.

HRMS (ESI): calcd. for C$_{32}$H$_{37}$NO$_7$Na [M+Na]$^+$ 570.2468; found 570.2472.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A method for preparing Et-743:

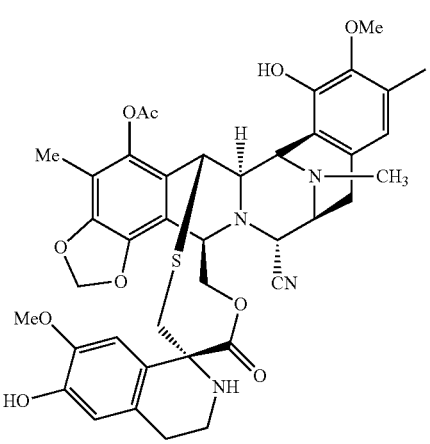

Et-743 wherein the method comprises the steps:

(g) subjecting compound 24 to the following reaction to obtain compound 25:

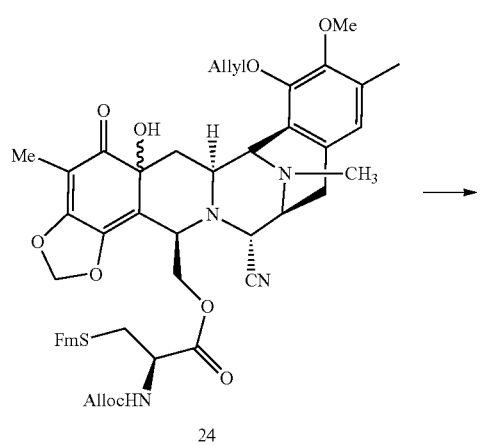

24

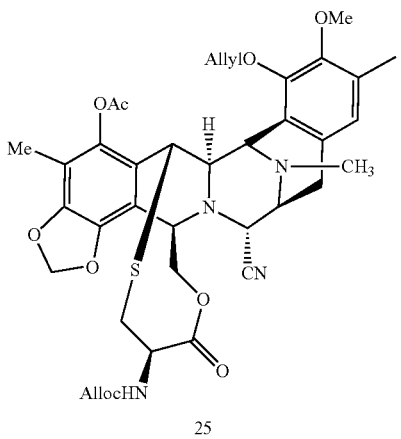

25 and preparing Et-743 from compound 25.

2. The method of claim 1, wherein further comprises the following step:

(f) reacting compound 22 with

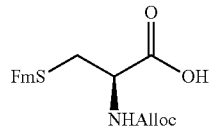

to obtain compound 24:

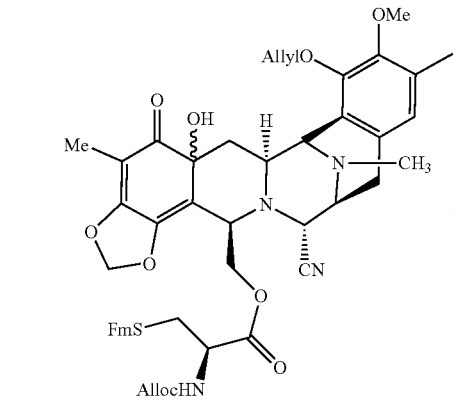

22

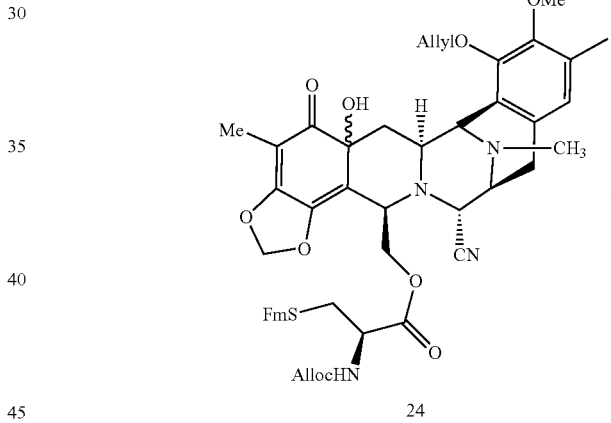

24

3. The method of claim 2, wherein further comprises the following step:

(e) subjecting compound 21 to the following reaction to obtain compound 22:

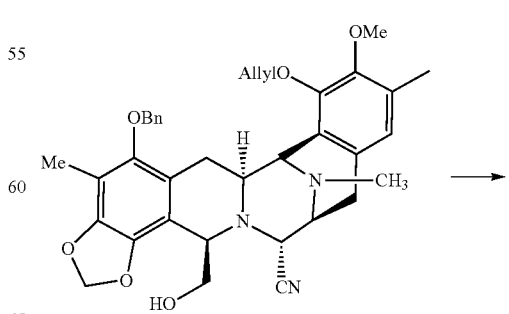

21

-continued

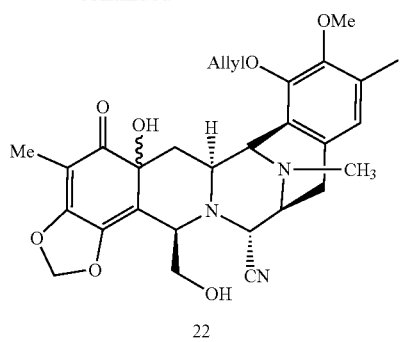

22

4. The method of claim 3, wherein further comprises the following step:

(d) subjecting compound 20 to the following reaction to obtain compound 21:

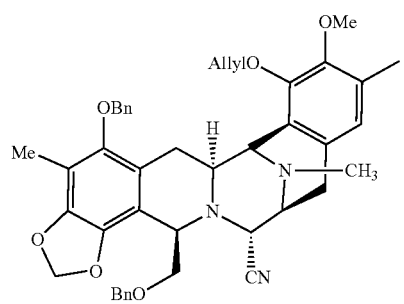

20

5. The method of claim 4, wherein further comprises the following step:

(c) subjecting compound 19 to the following reaction to obtain compound 20:

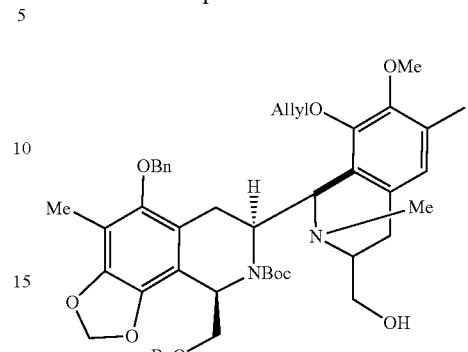

19

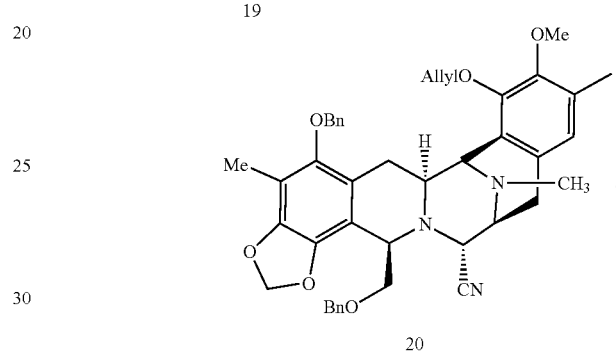

20

6. The method of claim 5, wherein further comprises the following step:

(b) subjecting compound 18 to the following reaction to obtain compound 19:

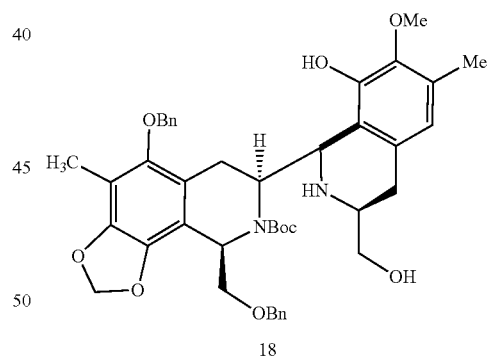

18

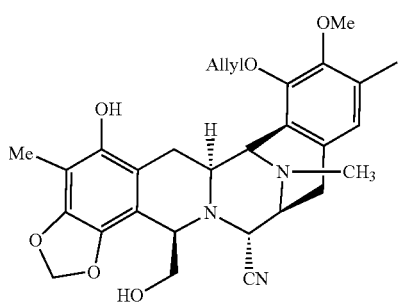

21

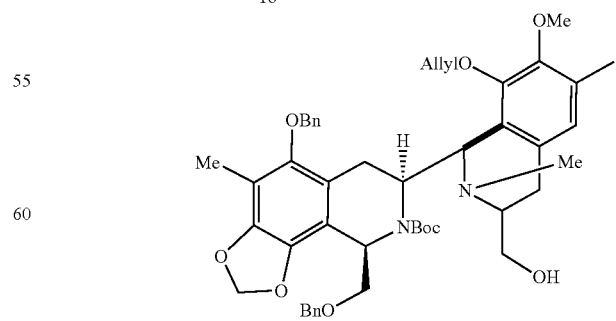

19

7. The method of claim 6, wherein further comprises the following step:
(a) reacting compound 9 with compound 16 to obtain compound 18:
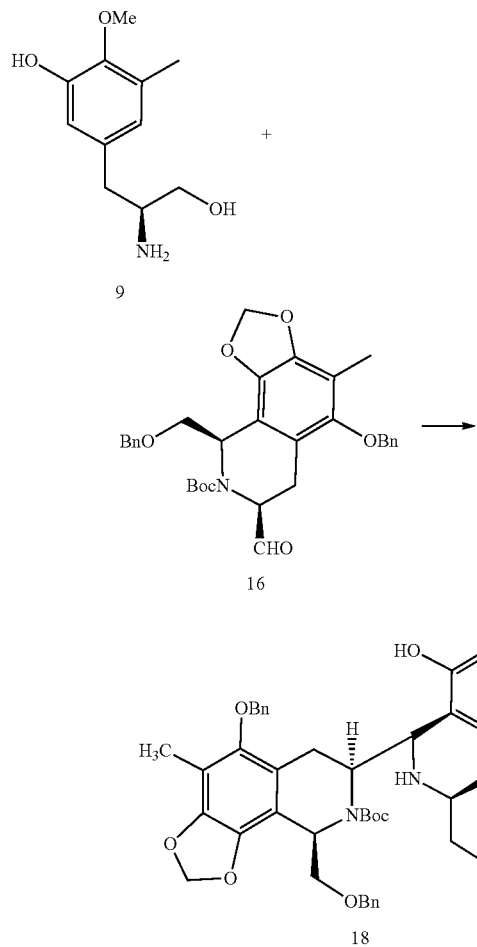
9
16
18
8. The method of claim 7, wherein further comprises the following step:
(vi) subjecting compound 15 to the following reaction to obtain compound 16:
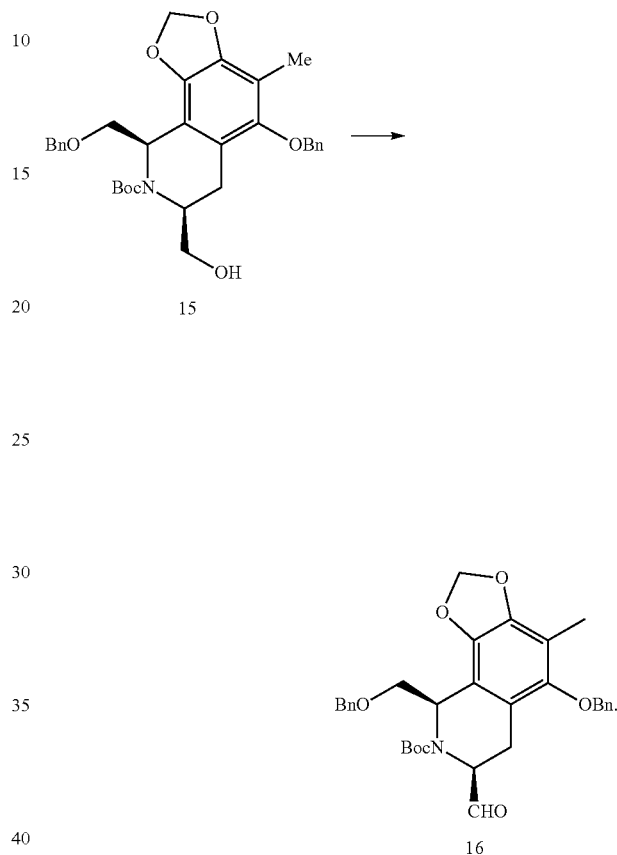
15
16
* * * * *